(12) United States Patent
Vidal et al.

(10) Patent No.: US 7,462,762 B2
(45) Date of Patent: Dec. 9, 2008

(54) METHOD FOR PRODUCING MODIFIED CARBON-BASED METABOLISM C₄ PLANTS BY OVEREXPRESSION OF PHOSPHOENOLPYRUVATE CARBOXYLASE

(75) Inventors: Jean Vidal, Gometz le Chatel (FR); Matthieu Jeanneau, Saint Valentin (FR); Pascual Perez, Chanonat (FR); Denise Gerentes, Le Crest (FR)

(73) Assignees: Biogemma, Paris (FR); Centre National de la Recherche Scientifique, Paris (FR)

( * ) Notice: Subject to any disclaimer, the term of this patent is extended or adjusted under 35 U.S.C. 154(b) by 551 days.

(21) Appl. No.: 10/473,966

(22) PCT Filed: Apr. 4, 2002

(86) PCT No.: PCT/FR02/01173

§ 371 (c)(1),
(2), (4) Date: Oct. 3, 2003

(87) PCT Pub. No.: WO02/081714

PCT Pub. Date: Oct. 17, 2002

(65) Prior Publication Data

US 2004/0103457 A1    May 27, 2004

(30) Foreign Application Priority Data

Apr. 4, 2001 (FR) .................... 01 04602
Nov. 16, 2001 (FR) .................... 01 14822

(51) Int. Cl.
| | |
|---|---|
| C12N 15/29 | (2006.01) |
| C12N 15/52 | (2006.01) |
| C12N 15/82 | (2006.01) |
| A01H 5/00 | (2006.01) |
| A01H 5/02 | (2006.01) |
| A01H 5/08 | (2006.01) |
| A01H 5/10 | (2006.01) |

(52) U.S. Cl. ............... 800/320.1; 800/287; 800/298; 800/320

(58) Field of Classification Search ............ 800/278, 800/284, 287, 290, 298, 320, 320.1; 536/23.1, 536/23.2, 23.6; 435/419, 320.1

See application file for complete search history.

(56) References Cited

U.S. PATENT DOCUMENTS

| | | | |
|---|---|---|---|
| 4,407,956 A | 10/1983 | Howell et al. | |
| 4,683,202 A | 7/1987 | Mullis | |
| 6,284,945 B1 * | 9/2001 | Dudits et al. | ............... 800/265 |
| 6,610,913 B1 * | 8/2003 | Arai et al. | ............... 800/320.2 |
| 2003/0115638 A1 | 6/2003 | Katsura et al. | |

FOREIGN PATENT DOCUMENTS

| | | |
|---|---|---|
| EP | 0 212 649 A2 | 3/1987 |
| EP | 0 723 012 A1 | 7/1996 |
| EP | 0 874 056 A1 | 10/1998 |
| EP | 0 916 725 A1 | 5/1999 |
| EP | 1 229 120 A1 | 7/2002 |
| JP | 212649 * | 3/1987 |
| WO | WO 98/49316 | 11/1998 |
| WO | WO 00/08187 | 2/2000 |
| WO | WO 00/28017 | 5/2000 |
| WO | WO 00/73475 * | 5/2000 |
| WO | WO 00/73475 | 12/2000 |
| WO | WO 01/18191 A2 | 3/2001 |

OTHER PUBLICATIONS

Hudspeth R. et al. Plant Physiology, 1992; vol. 98, pp. 458-464.*
Hudspeth R. et al. Plant Physiology, 1992, vol. 98; pp. 458-464.*
Tagu, D et al. Plant Cell Reports (1991) 9: 688-690.*
Hudspeth et al., *Plant Physiol.*, 98:458-464 (1991).
Kogami et al., *Transgenic Research*, 3:287-296 (1994).
Gehlen et al., *Plant Molecular Biology*, 32:831-848 (1996).
Ku et al., *Nature Biotechnology*, 17:76-80 (1999).
Lipka et al., *Plant Science*, 144:93-105 (1999).
Gonzalez et al., *Plant Physiol.*, 116:1249-1258 (1998).
Coursol et al., *The Plant Journal*, 23:497-506 (2000).
Hartwell et al., *The Plant Journal.*, 20(3):333-342 (1999).
Taybi et al., *Plant Physiol.*, 123:1471-1481 (2000).
Imaizumi et al., *Plant Molecular Biology*, 34:701-716 (1997).
Bandurski et al., *J. Biol. Chem.*, 204(2):781-786 (1953).
Cretin et al., *Nucleic Acids Research*, 18(3):658 (1990).
Wang et al., *J. Biol. Chem.*, 267(24):16759-16762 (1992).
Lepiniec et al., *Plant Molecular Biology*, 19:339-342 (1992).
McElroy et al., *Mol. Gen. Genet.*, 231:150-160 (1991).
Blechl et al., *Nature Biotechnology*, 14:875-879 (1996).
Kasuga et al., *Nature Biotechnology*, 17:287-291 (1999).
Depicker et al., *Journal of Molecular and Applied Genetics*, vol. 1, No. 6:561-573 (1982).
Franck et al., *Cell.*, 21:285-294 (1980).
An et al., *Plant Physiol.*, 81:86-91 (1986).
Guerche et al., *Mol. Gen. Genet.*, 206:382-386 (1987).
Finer et al., *Plant Cell Reports*, 11:323-328 (1992).
Hoekema et al., *Nature*, 303:179-180 (1983).

(Continued)

*Primary Examiner*—Russell Kallis
(74) *Attorney, Agent, or Firm*—Arent Fox LLP

(57) ABSTRACT

The invention relates to a method for producing a $C_4$-type plant having a modified carbon metabolism, comprising the following steps: an expression cassette, which comprises a nucleotide sequence that codes for a phosphoenolpyruvate carboxylase (PEPC), is introduced into at least one cell of plant $C_4$; the cell thus transformed is cultivated in such a way as to regenerate a $C_4$ plant containing said expression cassette in the genome thereof.

19 Claims, 9 Drawing Sheets

OTHER PUBLICATIONS

Robert et al., *The Plant Cell*, 1:569-578 (1989).
Armstrong, "Regeneration of Plants from Somatic Cell Cultures: Applications for In Vitro Genetic Manipulation", *The Maize Handbook*, M. Freeling, V. Walbot, eds., 1994 Springer-Verlag, New York, Inc., p. 663-671.
Barcelo et al., "Methods in Molecular Biology, vol. 49, Plant Gene Transfer Expression Protocols", Edited by H. Jones Humana Press, Inc., Totowa, NJ, p. 113-123.
Bligh et al., *Can. J. Biochem. Physiol.*, 37:911-917 (1959).
Brenner et al., *J. Mol. Biol.*, 202:913-915 (1988).
Sibbald et al., *Nucleic Acids Research*, 18:1063 (1990).
Pelleschi et al., *Plant, Cell, and Environment*, 20:493-503 (1997).
Ishida et al., *Nature Biotechnology*, 14:745-750 (1996).
Thomas et al., *Biochem. Biophys. Res. Comm.*, 143(1):170-177 (1987).
Smith et al., *Plant Physiol.*, 118:191-197 (1998).
Kausch et al., *Plant Molecular Biology*, 45:1-15 (2001).
Taniguchi et al., *Plant Molecular Biology*, 44:543-557 (2000).
"Giving a C4 Photosynthetic Circuit to a C3 Plant by Using a Malate Enzyme—by Transformation with a Gene" (JP11341928, XP-002185455—Abstract).
Tagu et al.: "Inheritance of Two Foreign Genes Co-Introduced into Petunia-Hybrid Direct Gene Transfer", *Plant Cell Tissue and Organ Culture*, 21(3):259-266 (1990), assigned to Japan Tobacco, Inc. (Abstract).
Tagu et al.: "Transciption of a Sorghum Phosphoenolpyruvate Carboxylase Gene in Transgenic Tobacco Leaves Maturation of Monocot Precursor Messenger RNA by Dicot Cells", *Plant Cell Reports*, 9(12):688-690 (1991) (Abstract).
Jeanneau et al., *Biochimie*, 84:1127-1135 (2002).
Jeanneau et al., *J. of Experimental Botany*, 376(376):1837-1845 (2002).
Jouanin et al., *Mol. Gen Genet.*, 206:387-392 (1987).
Database WPI, Section CH, Week 199720, Derwent Publications Ltd., London, GB; AN 1997-220420, XP002185462 & JP 09 065886 A, Japan Tafu Gurasu KK, Mar. 11, 1997.
D. Contour-Ansel et al., "Effect of Water Stress on Pyruvate, $P_i$ Dikinase and Phosphoenol Pyruvate Carboxylase Activities in the Leaves of Two Cultivars of Sorghum (Sorghum bicolor L.)", J. Agronomy & Crop Science, 1996, pp. 59-69, vol. 176.
Claude Cretin et al., "Production in *Escherichia coli* of active Sorghum phosphoenolpyruvate carboxylase which can be phosphorylated", Plant Molecular Biology, 1991, pp. 83-88, vol. 17.
Mireya Roderiguez-Penagos et al., "Response of Phosphoenolpyruvate Carboxylase from Maize Leaves to Moderate Water Deficit", J. Plany Physiol., 1999, pp. 631-638, vol. 155.
Denis Tagu et al., "Transcription of a sorghum phosphoenolpyruvate carboxylase gene in transgenic tobacco leaves: muturation of monocot PRE-mRNA by dicot cells", Plant Cell Reports, 1991, pp. 688-690, vol. 9.

* cited by examiner

METHOD FOR PRODUCING MODIFIED CARBON-BASED METABOLISM $C_4$ PLANTS BY OVEREXPRESSION OF PHOSPHOENOLPYRUVATE CARBOXYLASE

The present invention relates to a method for producing $C_4$ plants with modified carbon-based metabolism, conferring on them improved agronomic qualities.

Under limiting water conditions, $C_4$ plants have been able to adapt their carbon-based metabolism by concentrating the $CO_2$ content of the medium surrounding RUBISCO in order to promote the carboxylase activity of this enzyme to the detriment of its oxygenase activity (and its consequence: photorespiration), and therefore the photosynthetic yield. This mechanism involves the activity of the $C_4$ cycle, the first step of which is catalysed by a carboxylase, phosphoenolpyruvate carboxylase (PEPC EC 4.1.1.31), which has a high affinity for $CO_2$ (in hydrated form) and a high catalytic rate. $C_3$ plants, on the other hand, do not have such a system for concentrating $CO_2$, and photorespiration substantially limits the photosynthetic yield. In addition, in these plants, water use is less efficient (by a factor of 2). Thus, $C_4$ plants under conditions of water stress have a selective advantage compared with $C_3$ plants.

This explains the many studies published since 1992 aimed at overexpressing in $C_3$ plants a $C_4$-type PEPC in an attempt to increase the $CO_2$ concentration in the vicinity of RUBISCO and thus to limit photorespiration to the benefit of the photosynthetic yield and of the biomass (Hudspeth et al., 1992; Kogami et al., 1994; Gehlen et al., 1996; Ku et al., 1999; Lipka et al., 1999).

In the context of the present invention, the inventors have set out to provide a concept which is original with respect to previous studies since it is aimed at overexpressing a $C_4$-plant PEPC in a $C_4$ plant endogenously containing it, for the purpose of optimizing a carbon-based metabolism which is already very effective, and in particular under conditions of water stress. In the leaf, under normal conditions, it is a question of correcting a level of photorespiration which is moreover very low, and the expected impact of which on photosynthetic function is certainly limited in size. However, water stress leads to a significant decrease in the net assimilation of $CO_2$, in particular by reduction of the opening of the stomata. Under these growth conditions in which the water and the $CO_2$ availability are limiting, overexpression of PEPC might contribute to maintaining a concentration of the gas in the vicinity of RUBISCO which is greater than that of control plants and, as such, an improved assimilation of inorganic carbon.

Furthermore, there exists in all plants, $C_4$ or $C_3$ plants, various isoforms of the enzyme which in particular grace, besides the leaves, the roots and the grains. One of the major functions of these isoforms is devoted to maintaining the production of cellular energy when Krebs cycle intermediates (in particular a-ketoglutarate) are used by other metabolic pathways, such as the synthesis of amino acids (aspartate, glutamate and related amino acids). This "anaplerotic" function is in particular operational in grains, where it contributes to protein filling (Gonzalez et al., 1998; Macnicol et al., 1998). Moreover, in this organ, PEPC is involved in supplying the carbon-based backbones required for fatty acid synthesis, and also for developing lipid stores (Smith et al., 1992).

In the grain, the overexpression of PEPC is therefore liable to significantly improve protein- and lipid-filling capacity under normal conditions, if other limiting steps of the metabolic pathways concerned do not oppose this, more certainly under conditions of water stress which impair the functioning of wells and the plant's source-well relations. In this regard, it should also be underlined that a better photosynthetic capacity (due to overexpression of foliar PEPC) may have a positive impact on grains, the filling of which depends on a remobilization of the nitrogen and of the carbon in the leaves during maturation.

The invention aims to overcome the drawbacks of the prior art, and relates to a method for producing a $C_4$-type plant having a modified carbon-based metabolism, comprising the steps consisting in:
- introducing into at least one $C_4$ plant cell an expression cassette comprising a nucleotide sequence encoding a phosphoenolpyruvate carboxylase (PEPC);
- culturing the cell thus transformed so as to generate a $C_4$ plant containing said expression cassette in its genome.

The modified carbon-based metabolism is associated with overexpression or underexpression of PEPC compared with a nontransformed plant. Advantageously, the method relates to overexpression of PEPC in the regenerated transformed plants.

According to one embodiment, the method also comprises identifying and selecting the transformed cells capable of regenerating plants having a modified carbon-based metabolism compared with a nontransformed plant. Such a selection typically involves a marker gene.

Advantageously, said cell transformed according to the first step is also transformed with one or more nucleic acids chosen from:
- a nucleic acid encoding a protein component for modulation of the chain of transduction and phosphorylation of PEPC, such as, for example, a phosphoinositol phospholipase C (PIPLC) (Coursol et al., 2000) or a phosphoenolpyruvate carboxylase kinase (PEPCK) (Hartwell et al., 1999; Taybi et al., 2000);
- a nucleic acid encoding another protein of the $C_4$ cycle, such as, for example, pyruvate, phosphate dikinase (PPDK) (Imaizumi et al., 1997).

The expression "sequence encoding a PEPC" is intended to mean a sequence encoding an enzyme naturally expressed by a $C_4$ plant, which catalyses the virtually irreversible β-carboxylation of phosphoenolpyruvate in the presence of bicarbonate and a divalent cation, so as to form oxaloacetate and inorganic phosphate (Bandurski and Greiner, 1953). Among the types of PEPC found in $C_4$ plants, use may be made, according to the invention, of the nucleotide sequences encoding the enzymes of the $C_3$ PEPC form (anaplerotic function) or of the $C_4$ PEPC form (photosynthetic+anaplerotic function).

By way of example, mention may be made preferentially of the $C_4$ PEPC from sorghum (*Sorghum vulgare*) described by Crétin et al. (1990), having a nucleic acid sequence identical or homologous to the sorghum sequence SEQ ID No. 1.

Advantageously, use will be made of a nucleic acid comprising a nucleotide sequence chosen from:
a) the nucleotide sequence SEQ ID No. 1;
b) a nucleotide sequence homologous to the sequence of a) encoding a protein having phosphoenolpyruvate carboxylase activity;
c) a nucleotide sequence complementary to SEQ ID No. 1 or to a sequence defined in b);
d) a representative fragment of a sequence defined in a), b) or c);
e) a nucleotide sequence comprising a sequence as defined in a), b), c) or d); and
f) a modified nucleotide sequence of a nucleotide sequence as defined in a), b), c), d) or e).

Alternatively, use may be made of a mutated (Ser8/Asp8) $C_4$ PEPC (Wang et al., 1992) which has the (nonreversible) properties of the phosphorylated enzyme, which is the most effective form in terms of catalytic rate and of sensitivity to the inhibitor L-malate.

Advantageously, use may also be made of sequences encoding $C_3$ PEPCs, for example $C_3$ PEPCs having nucleic acid sequences identical or homologous to those described by Crétin et al. (1991) or Lepiniec et al. (1991).

The terms "nucleic acid", "nucleic acid sequence", "polynucleotide", "oligonucleotide", "polynucleotide sequence" and "nucleotide sequence", terms which will be used indifferently in the present description, are intended to denote a precise series of nucleotides, which may or may not be modified, making it possible to define a fragment or a region of a nucleic acid, which may or may not comprise unnatural nucleotides, and which may correspond equally to a double-stranded DNA, a single-stranded DNA and transcription products of said DNAs.

The expression "homologous nucleotide sequence" is intended to mean any nucleotide sequence which differs from the sequence SEQ ID No. 1 by substitution, deletion and/or insertion of a nucleotide or of a small number of nucleotides, at positions such that these homologous nucleotide sequences encode homologous polypeptides as defined below.

Preferably, such a homologous nucleotide sequence is identical to at least 75% of the sequence SEQ ID No. 1, preferably at least 85%, even more preferably at least 95%.

For the purpose of the present invention, the term "percentage identity" between two nucleic acid or amino acid sequences is intended to denote a percentage of nucleotides or of amino acid residues which are identical between the two sequences to be compared, obtained after best alignment, this percentage being purely statistical and the differences between the two sequences being distributed randomly and over their entire length. The term "best alignment" or "optimal alignment" is intended to denote the alignment for which the percentage identity determined as below is highest. Sequence comparisons between two nucleic acid or amino acid sequences are conventionally carried out by comparing these sequences after having aligned them optimally, said comparison being carried out by segment or by "window of comparison" so as to identify and compare local regions of sequence similarity. The optimal alignment of the sequences for the comparison may be carried out, besides manually, by means of the local homology algorithm of Smith and Waterman (1981, Ad. App. Math. 2: 482), by means of the local homology algorithm of Neddleman and Wunsch (1970, J. Mol. Biol. 48: 443), by means of the similarity search method of Pearson and Lipman (1988, Proc. Natl. Acad. Sci. USA 85: 2444), by means of computer programs using these algorithms (GAP, BESTFIT, BLAST P, BLAST N available on the NCBI site, FASTA and TFASTA in the Wisconsin Genetics Software Package, Genetics Computer Group, 575 Science Dr., Madison, Wis.). In order to obtain the optimal alignment, the BLAST program is preferably used, with the BLOSUM 62 matrix. The PAM or PAM250 matrices may also be used.

The percentage identity between two nucleic acid or amino acid sequences is determined by comparing these two sequences aligned in an optimal manner in which the nucleic acid or amino acid sequence to be compared may comprise additions or deletions with respect to the reference sequence for optimal alignment between these two sequences. The percentage identity is calculated by determining the number of identical positions for which the nucleotide or the amino acid residue is identical between the two sequences, dividing this number of identical positions by the total number of positions compared and multiplying the result obtained by 100 so as to obtain the percentage identity between these two sequences.

Preferentially, such a homologous nucleotide sequence hybridizes specifically to the sequence complementary to the sequence SEQ ID No. 1, under stringent conditions. The parameters which define the conditions of stringency depend on the temperature at which 50% of the paired strands separate (Tm).

For sequences comprising more than 30 bases, Tm is defined by the equation: Tm=81.5+0.41(% G+C)+16.6 Log (cation concentration)−0.63 (% formamide)−(600/number of bases) (Sambrook et al., Molecular Cloning, A laboratory manual, Cold Spring Harbor Laboratory Press, 1989, pages 9.54-9.62).

For sequences of less than 30 bases in length, Tm is defined by the equation: Tm=4(G+C)+2(A+T).

Under suitable conditions of stringency, under which aspecific sequences do not hybridize, the hybridization temperature is approximately 5 to 30° C., preferably 5 to 10° C., below Tm, and the hybridization buffers used are preferably solutions of high ionic strength such as a 6×SSC solution for example.

The term "nucleotide fragment" is intended to mean any fragment of the sequence SEQ ID No. 1, or of the nucleotide sequences homologous to the sequence SEQ ID No. 1, which encode(s) a peptide or a protein having phosphoenolpyruvate carboxylase enzymatic activity, as defined above. These nucleotide fragments have at least 15 consecutive nucleotides, preferably at least 30, 75, 150, 300 and 450 consecutive nucleotides, of the sequence from which they are derived.

The term "modified nucleotide sequence" is intended to mean any nucleotide sequence obtained by mutagenesis according to techniques well known to those skilled in the art, and comprising modifications compared to the normal sequences, for example mutations in the regulatory and/or promoter sequences for expression of the polypeptide, in particular leading to a modification of the level of expression or of the activity of said polypeptide.

The term "modified nucleotide sequence" is also intended to mean any nucleotide sequence encoding a modified polypeptide.

The representative fragments according to the invention may also be probes or primers, which may be used in methods for detecting, identifying, assaying or amplifying nucleic acid sequences. These methods may involve amplification techniques of the PCR (described, for example, in the document U.S. Pat. No. 4,683,202) or PCR-like type, such as, for example, the SDA (strand displacement amplification) technique (Walker et al., 1992, Nucleic Acids Res. 20: 1691), the TAS (transcription-based amplification system) technique described by Kwoh et al. (1989, Proc. Natl. Acad. Sci. USA, 86, 1173), the 3SR (self-sustained sequence replication) technique described by Guatelli et al. (1990, Proc. Natl. Acad. Sci. USA 87: 1874), the NASBA (nucleic acid sequence based amplification) technique described by Kievitis et al. (1991, J. Virol. Methods, 35, 273), the TMA (transcription mediated amplification) technique, the LCR (ligase chain reaction) technique described by Landegren et al. (1988, Science 241, 1077), the RCR (repair chain reaction) technique described by Segev (1992, Kessler C. Springer Verlag, Berlin, N.Y., 197-205), the CPR (cycling probe reaction) technique described by Duck et al. (1990, Biotechniques, 9, 142), and the Q-beta-replicase amplification technique described by Miele et al. (1983, J. Mol. Biol., 171, 281).

For the purpose of the invention, a probe or primer is defined as being a single-stranded nucleic acid fragment or a denatured double-stranded fragment comprising, for example, from 12 bases to a few kb, in particular from 15 to a few hundred bases, preferably from 15 to 50 or 100 bases, and having a specificity of hybridization under given conditions so as to form a hybridization complex with a target nucleic acid.

According to one embodiment of the invention, the nucleic acid encoding the PEPC protein is inserted in the sense orientation into a nucleic acid construct, called expression cassette or construct, and is linked to elements which allow its expression and, optionally, its regulation. A DNA expression cassette can be prepared by those skilled in the art in various suitable ways. A DNA construct typically includes 5' and 3' regulatory sequences functionally linked to the PEPC gene. The term "functionally linked" refers to a functional link between the 5' and 3' regulatory sequences and the nucleic acid sequence being controlled. The 5' regulatory sequence is typically a selected promoter. Controlled transcription by a functionally linked promoter produces a functional messenger RNA, the transcription of which produces the PEPC. An expression cassette typically comprises a nucleic acid sequence for PEPC linked, in a manner which is functional in the transformed plant, to a transcription initiation region (a promoter sequence) and to a transcription termination region.

Among the promoters, use may preferentially be made of a constitutive promoter, such as the rice actin promoter followed by the rice actin intron (RAP-RAI) contained in the plasmid pAct1-T.609796068949642 (McElroy et al., 1991) or the 35S promoter (Kay et al., 1987), or a tissue-specific promoter. Advantageously, use may be made of the wheat high molecular weight glutenin HMGW promoter (Blechl et al., 1994) or the PEPC promoter of the sorghum phosphoenolpyruvate carboxylase gene (Crétin et al., 1991), which allow, respectively, expression of the protein of interest in the seeds or the leaves. Promoter sequences which induce expression under conditions of water stress (Kasuga et al., 1999) may also be used. Among the terminators which can be used in the constructs of the invention, mention may be made in particular of the 3' end of the *Agrobacterium tumefaciens* nopaline synthase gene (Depicker et al., 1982). Mention may also be made of the 35S polyA terminator of the cauliflower mosaic virus (CaMV), described in the article by Franck et al. (1980).

The expression of the PEPC protein can also be regulated using suitable sequences such as:
  introns, for example the maize adh1S intron 1 (Callis et al., 1987), the tobacco yellow mosaic DSV intron (Morris et al., 1992), and the rice actin-1 intron (McElroy et al., 1990);
  enhancer sequences, for example the transcription activator of the tobacco mosaic virus TEV (Carrington and Fred—1990);
  leader sequences, for example the EMCV leader (Encephalomyocarditis 5' noncoding region) (O. Elroy-Stein, T. R. Fuerest, and B. Moss (1989) *PNAS USA,* 86: 6126-6130), the TEV (tobacco etch virus) leader (Allison et al. (1986)); the MDMV (maize dwarf mosaic virus) leader (*Virology,* 154: 9-20); the BiP-human binding protein leader (D. G. Macejack and P. Sarnow (1991) *Nature,* 353: 90-94), the AMV RNA 4 leader (S. A. Jobling and L. Gehrke, (1987) *Nature,* 325: 622-625), and the TMV leader (D. R. Gallie et al. (1989) *Molecular Biology of RNA,* pages 237-256).

A subject of the invention is also a vector comprising an expression cassette defined above.

According to one embodiment, the expression cassette is inserted into a nucleotide vector, such as a plasmid, which may also comprise a marker gene, for example a gene for selecting a transformed plant from a plant which does not contain the transfected foreign DNA. As a marker gene, mention may be made of a gene which confers resistance to an antibiotic, for example to hygromycin (Herrera-Estrella et al., 1983), or resistance to a herbicide such as the sulphonamide asulam (WO 98/49316). Use will preferably be made of the coding sequence of the *Streptomyces hygroscopicus* Bar gene (accession No. X 17220) encoding a phosphinotricine acetyltransferase which detoxifies phosphinotricine (selective agent of the herbicide Basta/Liberty®) by acetylation (White et al., 1990).

The plant cells are transformed with a vector as defined above, transferred into a cellular host capable of infecting said plant cells, allowing integration into the genome of the latter of the nucleotide sequences of interest initially contained in the genome of the abovementioned vector. Advantageously, the cellular host used is a bacterial strain, such as *Agrobacterium tumefaciens,* in particular according to the method described in the article by An et al. (1986), or *Agrobacterium rhizogenes,* in particular according to the method described in the article by Guerche et al. (1987). By way of example, the transformed cells are typically cells from calluses, from embryos, from meristematic cells and/or from cell cultures in suspension.

The transformation of the plants can be obtained by various suitable techniques known to those skilled in the art, for example described in *Methods in Enzymology* Vol. 153 ("Recombinant DNA Part D"), 1987. The term "transformation" refers to a genetic manipulation of a plant, of a cell, of a cell line, of a callus, of a tissue, of a part of a plant, or the like. Such an element is transformed in the presence of a recombinant DNA which is introduced into the genetic material of this element, chromosomally or extrachromosomally. The recombinant DNA may be a foreign DNA, a heterologous DNA or a chimeric DNA. The recombinant DNA may be included randomly or in a way which is targeted to a specific site of a homologous recombination, according to techniques known to those skilled in the art.

For example, the plant cells can be transformed by transferring the T region of the tumour-inducing extrachromosomal circular Ti plasmid of *Agrobacterium tumefaciens,* using a binary system (Watson et al., 1994). To do this, two vectors are constructed. In one of these vectors, the T region has been removed by deletion, with the exception of the left and right borders, a marker gene being inserted between them to allow selection in the plant cells. The other partner of the binary system is an auxiliary Ti plasmid, which is a modified plasmid which no longer has a T region but which still contains the vir virulence gene necessary for transformation of the plant cell.

According to a preferred mode, it is possible to use the method described by Ishida et al. (1996), for the transformation of monocotyledons.

Mention may also be made of other embodiments for introducing the expression cassette into a plant cell, in particular the methods of direct transfer of genes into plant cells, such as direct microinjection into plant embryoids (Neuhaus et al., 1987), infiltration under vacuum (Bechtold et al., 1993) or electroporation (Chupeau et al., 1989), or else direct precipitation with PEG (Schocher et al., 1986) or bombardment, with a gun, of particles covered with the plasmid DNA of interest (Fromm et al., 1990).

According to another protocol, the transformation is carried out according to the method described by Finer et al. (1992), using a particle gun with particles of tungsten or of gold.

The cauliflower mosaic virus (CaMV) may also be used as a vector for introducing the foreign nucleic acid into the plant cells (Hohn et al., (1982) "Molecular Biology of Plant Tumors", Academic Press, New York, pp. 549-560; Howell, U.S. Pat. No. 4,407,956). The CaMV viral DNA is inserted into a parent bacterial plasmid, creating a recombinant DNA molecule which can be multiplied in the bacterium. After cloning, the recombinant plasmid can again be cloned and then modified by introducing the desired DNA sequence at a unique restriction site. The modified viral portion of the recombinant plasmid is then cut out from the parent bacterial plasmid and used to inoculate plants or plant cells.

A subject of the invention is also a host cell transformed with the nucleic acid sequences described above, and also a plant or a part of a plant, in particular fruit, seed, grain, pollen, leaf or tuber, which can be obtained using one of the methods set out above. The descendants or a clone of such plants are also part of the invention.

They may be field crop plants or vegetables and flowers, which belong to $C_4$-type plants, such as maize and sorghum.

The hybrid transgenic plants obtained by crossing at least one plant according to the invention with another are also part of the invention.

The expression cassette is typically stably integrated into the genome of the cell.

According to another aspect, a subject of the invention is also:
- the use of a nucleic acid encoding a PEPC protein, for producing a $C_4$-type transgenic plant with a modified content of carbon-based assimilates, promoting fruit maturation and seed filling;
- the use of a nucleic acid encoding a PEPC protein, for producing a $C_4$-type transgenic plant with a modified content of carbon-based assimilates, conferring on it better tolerance to water stress.

According to another aspect, a subject of the invention is also the use of a nucleic acid encoding a PEPC protein, or a fragment thereof, as a probe or a primer for amplification, for selecting transformed- plants as described above, exhibiting better resistance to water stress and/or modified grain filling.

The invention relates in particular to a plant exhibiting an increase in expression of the PEPC protein compared with a nontransformed plant, a 2- to 3-fold increase for example, in the leaves and in the grains.

The overexpression of PEPC in the transformed plants makes it possible to concentrate $CO_2$ at the site of RUBISCO and to facilitate assimilation of $CO_2$ despite its poor availability under conditions of water stress (reduced opening of the stomata). The authors of the present application have shown that it is possible to improve the assimilation of $CO_2$ (carboxylase activity) under conditions of water stress: specifically, overexpression of PEPC under conditions of water stress and for high resistance of stomata makes it possible to increase photosynthetic carbon flow and Rubisco activity.

This better tolerance to water stress of the transformed plants according to the invention, compared to the control plants, can be measured using physiological, morphological and/or biochemical methods. By way of example, mention may be made of measurements of PEPC activity (functional properties), of PEPCk activity and of the level of phosphorylation of PEPC in planta, measurements of net assimilation of. $CO_2$, of $CO_2$ compensation point and of photosynthetic efficiency in a $CO_2$-depleted atmosphere, measurements of efficiency of water use, and measurements of fresh weight and dry weight, under normal conditions and conditions of water stress.

The invention also relates to an increase in expression of the PEPC protein (photosynthetic and anaplerotic function) conferring on the transformed plants a modified content of carbon-based assimilates, promoting grain filling.

This modification of grain filling in the transformed plants according to the invention, compared to the nontransformed plants, can be measured using morphological, physiological and/or biochemical methods. By way of example, mention may preferentially be made of infrared spectrophotometry techniques, gasphase elemental analysis techniques (method of Dumas by combustion and gas chromatography) or lipid analysis techniques (Metcalfe et al., 1966; Bligh and Dyer, 1959).

The use of a nucleic acid encoding a PEPC, or a fragment thereof, as a probe or a primer for a PCR-type amplification, for selecting transformed plants having a modified carbon-based metabolism, and therefore exhibiting better tolerance to water stress and modified grain filling, also falls within the context of the invention.

The nucleic acid sequence encoding a PEPC, such as that designated SEQ ID No. 1, and also any oligonucleotide obtained from this sequence, can thus be used as a probe in marker-assisted selection programmes, for example in order to follow the introgression of the gene encoding the PEPC protein in a plant. For this, at least one of these probes is labelled, for example with a radioactive isotope, and then brought into contact with genomic DNA of the plant, digested beforehand with restriction enzymes, under conditions which allow specific hybridization of the labelled probe to the DNA in question.

It is also possible to use a nucleic acid encoding a PEPC protein, or a fragment thereof, as a probe or a primer for amplification, for selecting plants naturally overexpressing a PEPC and therefore exhibiting better resistance to water stress and/or modified grain filling.

Other advantages of the invention will become apparent during the following description, illustrated by the drawings in which.

EXAMPLES

1—Construction of Recombinant Vectors

A sorghum PEPC cDNA ($C_4$ plant) was isolated according to a method described in the literature (Crétin et al., 1990). The accession number of the complete sequence of the sorghum (cv Tamaran) $C_4$-form PEPC cDNA is: X17379.

First, 4 basic plasmid vectors, pMj-26, pMj-19, pMj-30 and pMj-31, are constructed, containing respectively the PEPC promoter, or the 35S promoter, or the actin promoter-actin intron (pAct), or the HMWG promoter, with the cDNA of the PEPC gene in all these constructs and also the nopaline synthase terminator (terNos) which introduces a polyadenylation signal which is functional in many plant species.

Intermediate vectors are then prepared for homologous recombination with the Japan Tobacco vector pSB1 (EP 672 752) in *Agrobacterium tumefaciens* strain LBA 4404 (Hoekema et al., 1983).

The transfer followed by the expression of the genes (gene for selection and gene of interest) in maize is based on the natural properties of *Agrobacterium tumefaciens* (Zambrisky et al., 1989) and on the strategy of the superbinary plasmid (Hiei et al., 1994 and Ishida et al., 1996).

The restriction enzymes used for the clonings are provided by New England Biolabs (New England Biolabs, UK). The enzymatic reactions are carried out by following the protocols described by Sambrook et al., in the manual Molecular cloning (Molecular cloning: A Laboratory Manual, 1989, Cold Spring Harbor Laboratory Press, Cold Spring Harbor, N.Y.).

1-1—Basic Plasmid Vectors

1-1-1—The Construct pMJ-26: pPEPC-PEPC

Figure 1:
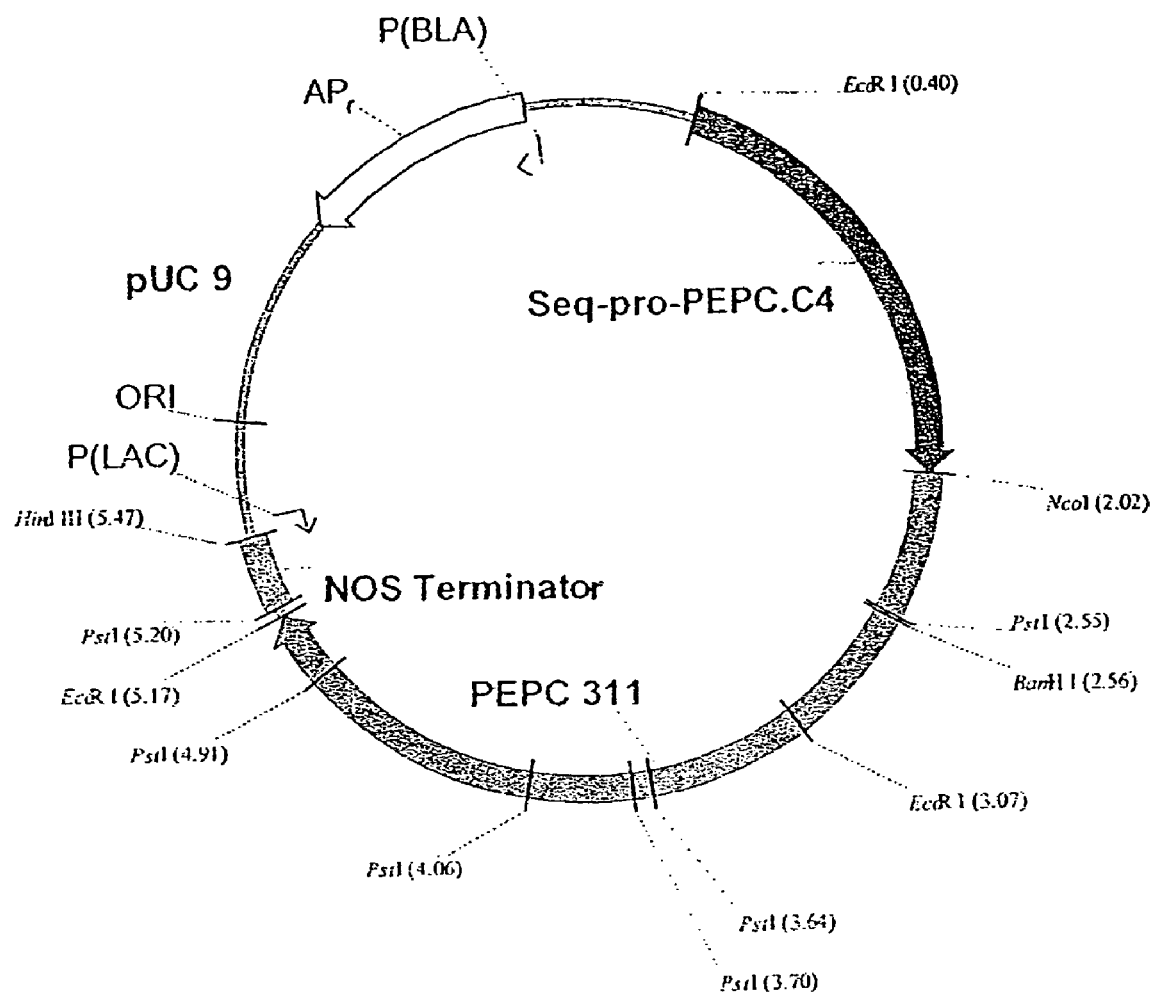
FIG. 1 represents a restriction map of the plasmid pMj26 containing the construct proPEPc~PEPC311~Nos PolyA.

The Nos terminator (0.4 kb BamHI/HindIII insert) of pCaMVNeo (Fromm et al., 1986) is cloned into the plasmid pUC9 (Vieira and Messing, 1982) digested with BamHI and HindIII. The plasmid is opened with BamHI and the ends are made blunt with Klenow polymerase. The PEPC cDNA CP311 (SmaI/HindIII insert made blunt-ended by filling with Klenow polymerase, comprising a silent mutation at the ATG+120 bp NcoI site; Wang et al., 1992) is ligated thereto. The orientation of the Nos terminator and of the cDNA and their junction are verified by digestions and sequencing. The 1 530 bp NcoI insert of the genomic clone CP46 (Lepiniec et al., 1992), the complete sequence of which is given below in SEQ ID No. 2 (promoter sequence proPEPc), is cloned at the NcoI site of the plasmid previously obtained. The orientation is verified by digestions and sequencing. The map of pMJ-26 is given in FIG. 1.

1-1-2—The Construct pMJ-19: p35S-PEPC

Figure 2:
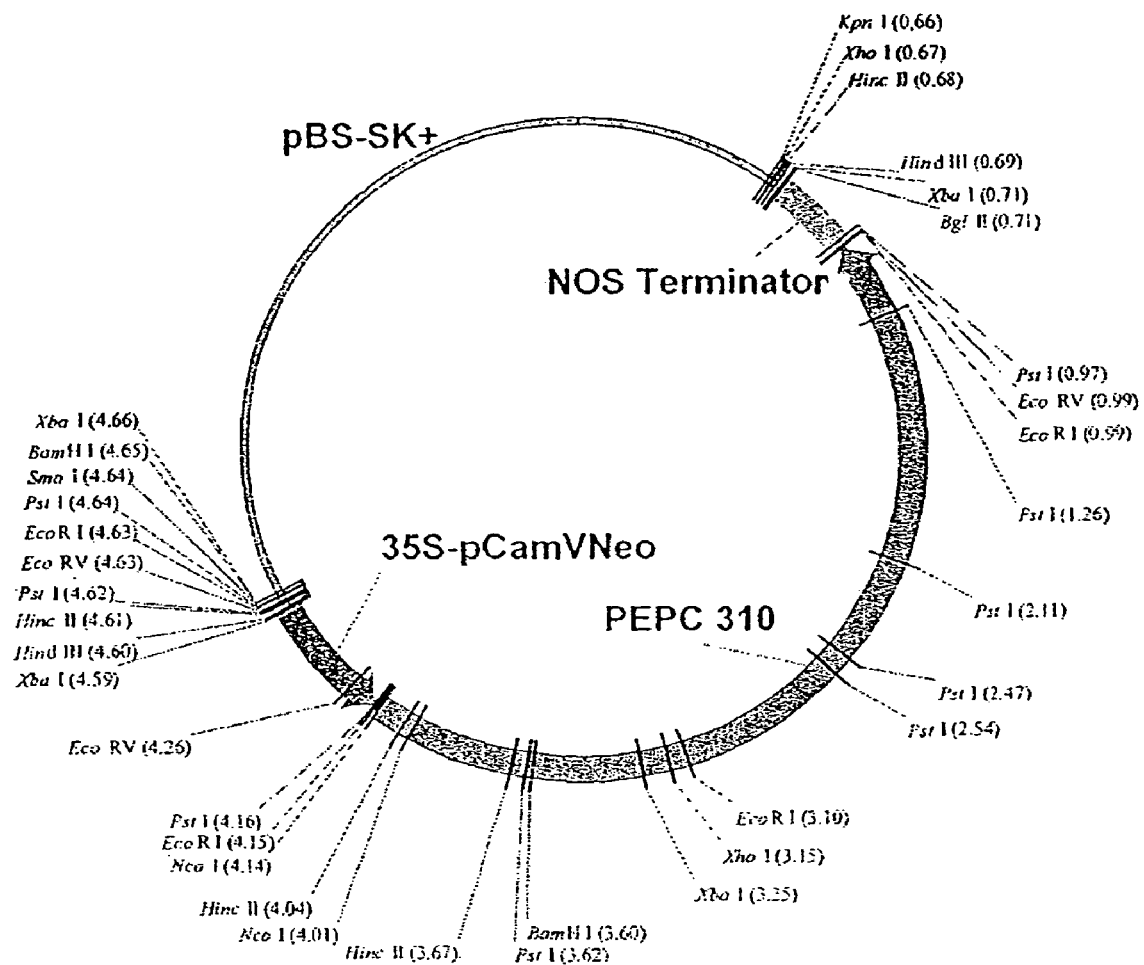
FIG. 2 represents a restriction map of the plasmid pMj19 containing the construct 35S~PEPC310~Nos PolyA.

The PEPC cDNA CP310 (SmaI/HindIII insert made blunt-ended by filling with Klenow polymerase, Crétin et al., 1991) is cloned at the BamHI site of pCaMVNeo made blunt-ended, between the 35S promoter (0.4 kb) and the Nos terminator (0.25 kb). The HindIII insert (3.7 kb) is then cloned at the HindIII site of pSK+ (Genbank No. 52325). The orientation of the 35S promoter and of the cDNA and also their junction are verified by digestions and sequencing. The map of pMJ-19 is given in FIG. 2.

1-1-3—The Construct pMj-30: pActin intron-PEPC

Figure 3:
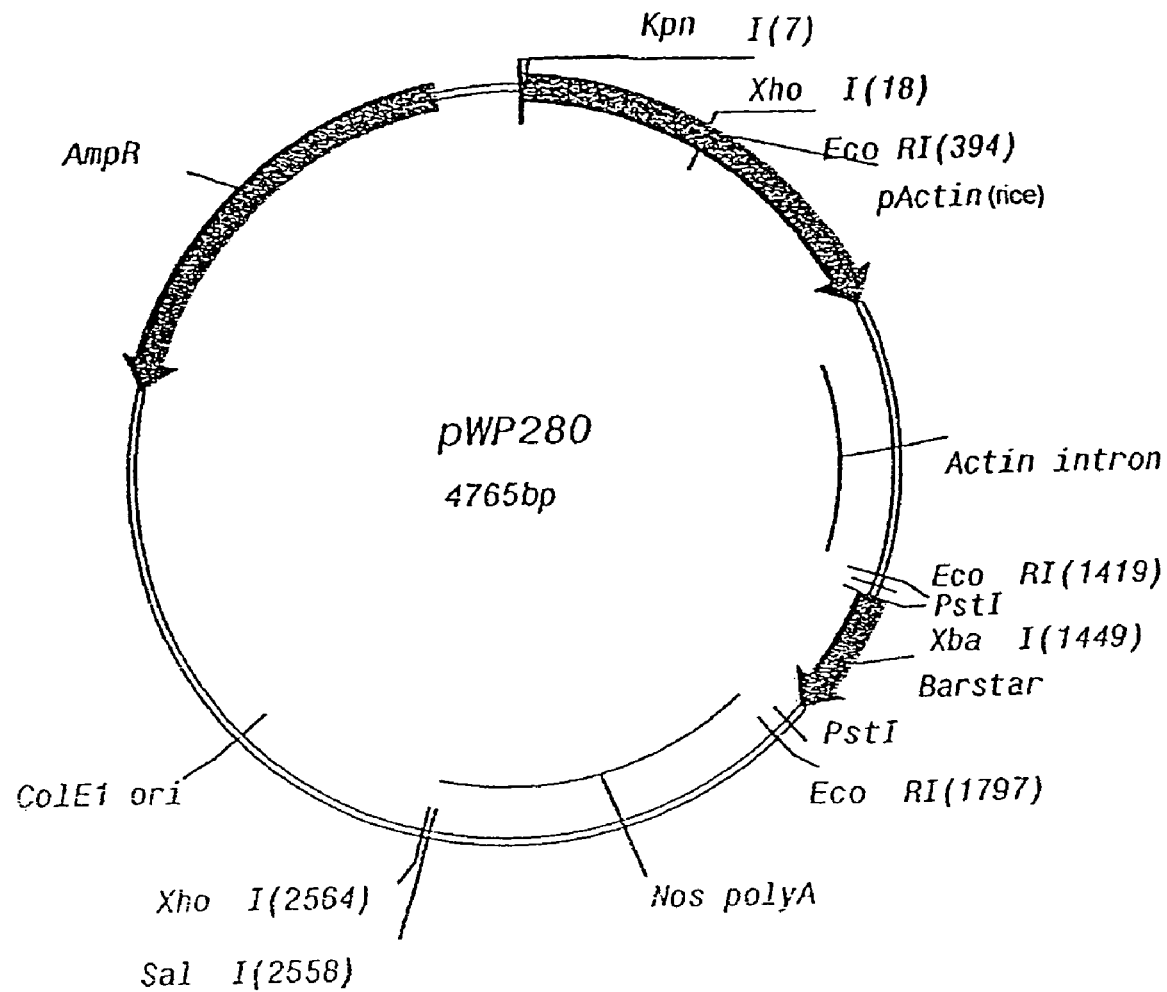
FIG. 3 represents a restriction map of the plasmid pWP280 containing the construct pActin intron~barnase~Nos PolyA.

The cloning of the construct actin promoter~PEPC~Nos 3' uses, as basic plasmid, the plasmid pWP280 containing the cassette pActin-intron~Barstar~Nos polyA (FIG. 3), in which the Barstar fragment is replaced with the PEPC fragment.

The basic plasmid was obtained according to the following steps: the barstar gene (Hartley, 1988, J. Mol. Biol., 202, 913-915) was transferred, as an XbaI/HincII fragment, into an XbaI/SmaI site of the plasmid pW90, derived from the plasmid pJIT30 described by Guérineau et al., 1990, Plant Mol. Biol., 15: 127-136) (CaMV 35S promoter replaced with the double 35S promoter and the polylinker region between the XbaI and EcoRI sites replaced with the SpeI, BamHI, SmaI and PstI sites). The CaMV polyA region of the plasmid obtained is replaced with the polyA region of pED23 (Dale et al., 1990, Gene, 91: 79-85), forming the plasmid pWP266. The double CaMV 35S promoter region is finally replaced with the rice actin promoter and intron derived from pCOR113 (McElroy et al., 1991, Mol. Gen. Genet., 231: 150-160) forming the plasmid pWP280.

Figure 4:
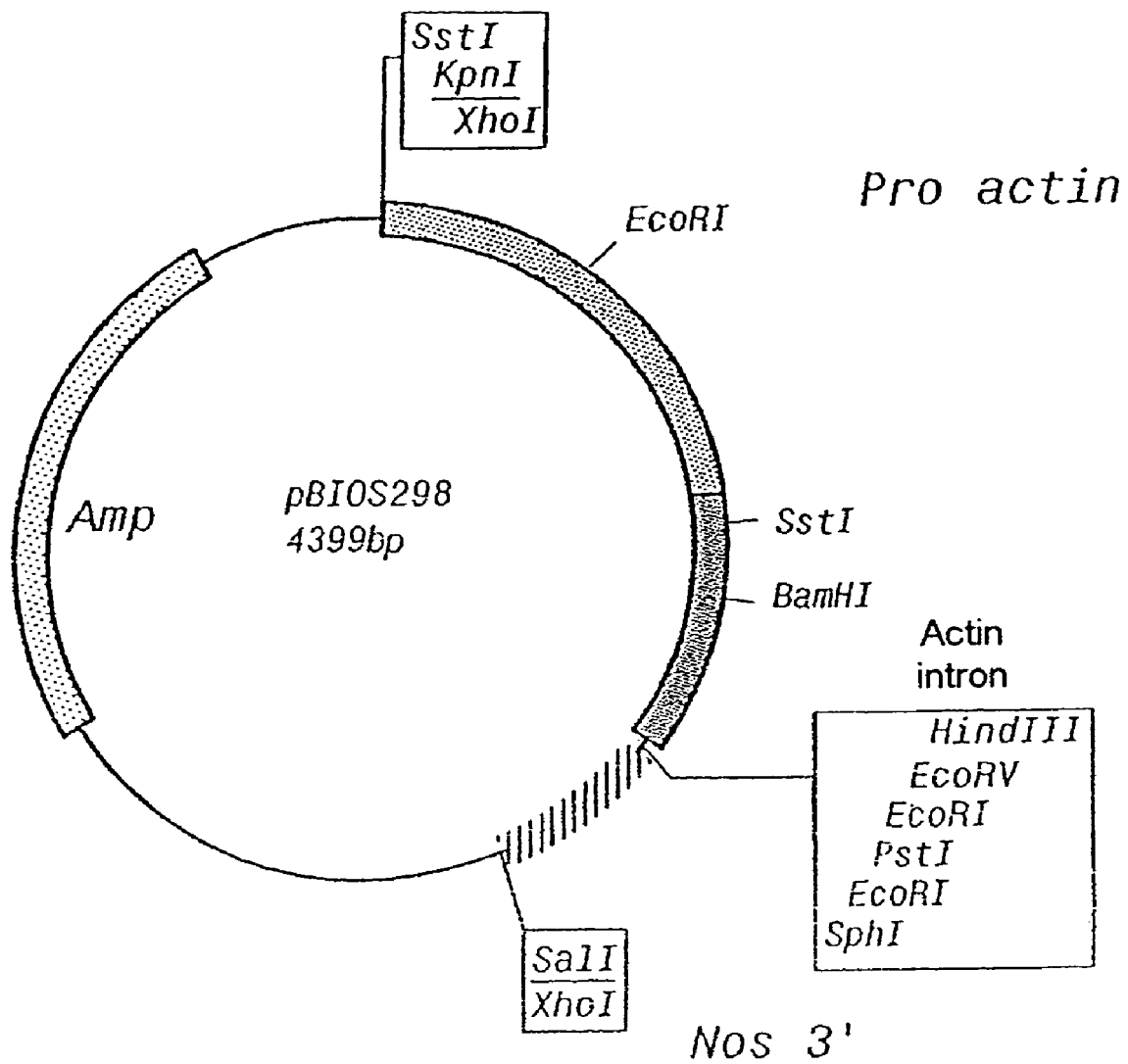
FIG. 4 represents a restriction map of the plasmid pBIOS298 containing the construct pActin intron~multiple clonage site~Nos PolyA.
Figure 5:
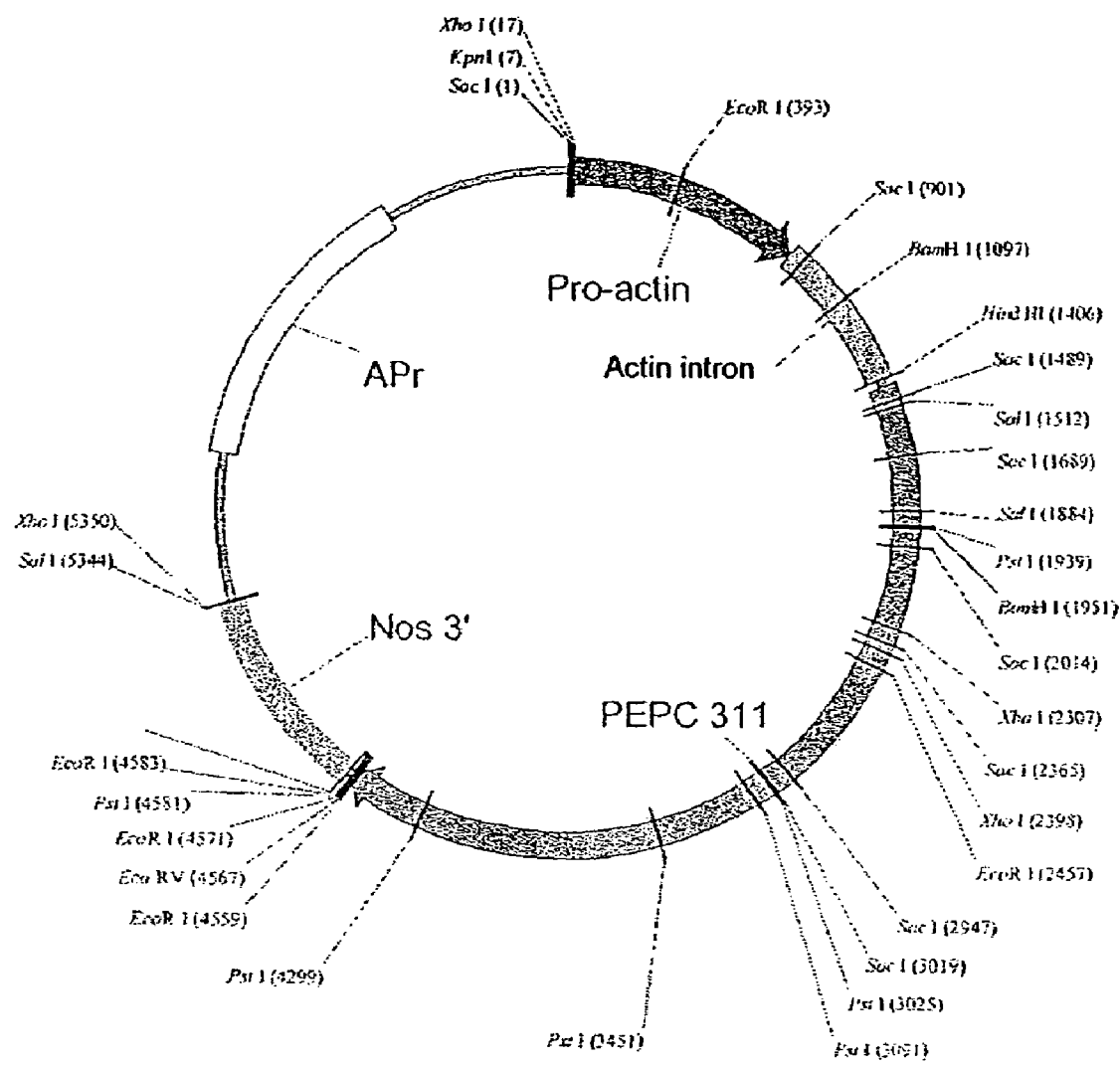
FIG. 5 represents a restriction map of the plasmid pMj30 containing the construct pActin intron~PEPC311~Nos PolyA.

The barstar fragment was then excised from this plasmid pWP280 by digestion with the enzyme PstI, and then religated on itself to give the vector pBIOS298 containing the fragment actin promoter-intron~multiple cloning site~Nos3' terminator (FIG. 4). The construct pBIOS-298 is opened at the EcoRV site between the actin intron and the Nos terminator, and then dephosphorylated. The NcoI-EcoRV insert of pMJ-26 is made blunt-ended by filling with Klenow polymerase and then cloned at the site of pBIOS-298. The orientation of the construct was verified by digestion and the actin intron-PEPC junction was sequenced. The map of pMJ-30 is given in FIG. 5.

1-1-4—The Construct pMj-31: pHMWG-PEPc

The vector pBL3214 is derived from a plasmid pBluescript II SK+ (Stratagene) into which the wheat HMWG (high molecular weight glutenin) promoter sequence (Robert et al., 1989), specific for the seed albumen, and an *Agrobacterium tumefaciens* Nos 3' terminator sequence (Depicker et al., 1982), have been inserted, by choosing specific restriction enzymes, which is within the scope of those skilled in the art.

Figure 6:
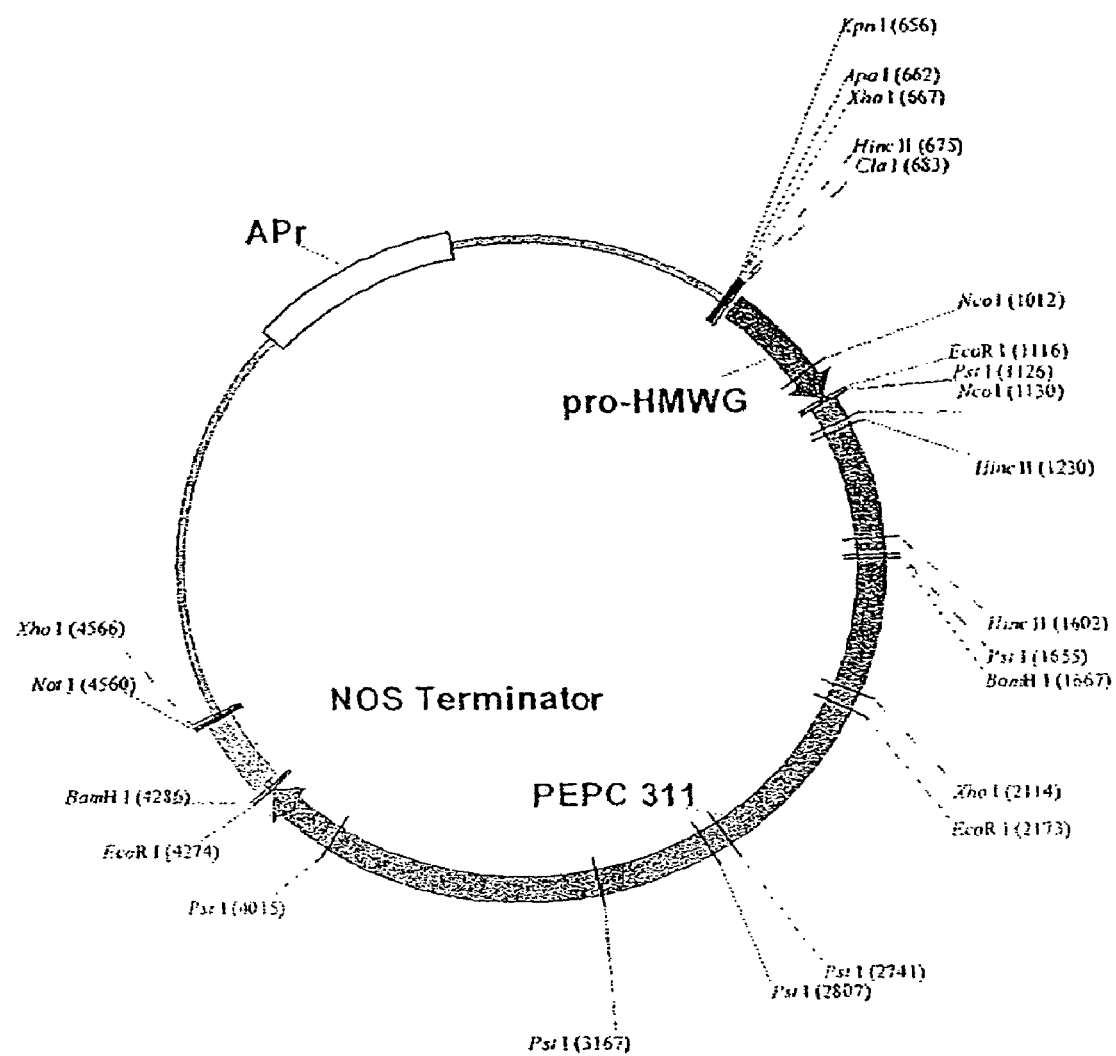
FIG. 6 represents a restriction map of the plasmid pMj31 containing the construct pHMWG~PEPC311~Nos PolyA.

The construct pBL3214 is opened at the SmaI site between the HMWG promoter and the Nos terminator, and then dephosphorylated. The NcoI-EcoRV insert of pMJ-26 is made blunt-ended by filling with Klenow polymerase, and then cloned at the site of p3214. The orientation of the construct was verified by digestion and the pHMWG-PEPC junction was sequenced. The map of pMJ-31 is given in FIG. 6.

1-2—Construction of the Intermediate Vectors for Homologous Recombination with pSB1 (Production of Superbinary Plasmids)

The vectors used for the homologous recombination in *Agrobacterium tumefaciens* are derived from the vector pBIOS 273.

1-2-1—Construction of the Plasmids pBIOS 273, 274, and 308

The Basic Vector for the Homologous Recombination is the Vector pBIOS 273. This Vector was Generated in 2 Steps:

cloning of the BspDI/XhoI fragment (p-Act-Bar-terNos) of the vector pDM 302 (Cao et al., 1992) into the SmaI and BspDI sites of the vector pSB12 (Japan Tobacco). The vector resulting from this cloning is called pBIOS 272.

deletion of the XhoI site at position 3363 of the vector pBIOS 272 by partial digestion with XhoI and action of DNA polymerase I large (Klenow) fragment. The vector obtained, which has a unique XhoI site, is named pBIOS 273.

Construction of the Plasmid pBIOS 274 cloning of the XhoI fragment (Pro A9-Barnase-terCaMV) of the vector pWP 128 (Paul et al., 1992) into the XhoI-restricted pBIOS 273 vector.

Construction of the Plasmid pBIOS 308 pBIOS 308 derives from pBIOS 306, which was obtained by cloning the 795 bp [lacuna] I/XhoI fragment (Asr1 cDNA) into the previously described vector pBIOS 298, restricted with ECOR V.

cloning of the 2 970 bp SalI/XhoI fragment of the vector pBIOS 306 into the BspDI/XhoI sites of the vector pBIOS 274 generates pBIOS 308.

1-2-2—Generation of the Intermediate Recombination Vectors Containing the PEPC cDNA These constructs were generated from the vectors pBIOS 274, pBIOS 273 and pBIOS 308.

The Vector pBIOS 326

This vector was obtained by cloning the ApaI/BstBI fragment of the vector pMJ-30 into the PmeI/BstBI sites of the vector pBIOS 308.

The Vector pBIOS 327

This vector was obtained by cloning the XhoI fragment of the vector pMJ-31 into the XhoI sites of the vector pBIOS 274.

The Vector pBIOS 356

This vector was obtained by cloning the SmaI/HindIII fragment of the vector pMJ-26 into the PmeI sites of the vector pBIOS 273.

2—Transformation of Maize 2-1—Particle Gun

The method used is based on the use of a particle gun identical to that described by J. Finer (1992). The target cells are rapidly dividing undifferentiated cells which have conserved an ability to regenerate whole plants. This type of cell makes up the maize embryogenic callus (termed type II callus). These calluses are obtained from immature embryos of the HiII genotype according to the method and on the media described by Armstrong (Maize Handbook; 1994 M. Freeling, V. Walbot Eds; pp. 665-671). These fragments of calluses, with a surface area of 10 to 20 mm$^2$, were placed, 4 h before bombardment, in a proportion of 16 fragments per dish, at the centre of a Petri dish containing a culture medium identical to the callus initiation medium, supplemented with 0.2 M of mannitol+0.2 M of sorbitol. The plasmids described in the preceding examples and carrying the PEPc sequences to be introduced are purified on a Qiagen® column according to the manufacturer's instructions. They are then precipitated onto particles of tungsten (M10) according to the protocol described by Klein (1987). The particles thus coated are projected onto the target cells using a gun and according to the protocol described by Finer (1992). The dishes of calluses thus bombarded are then sealed with Scellofrais® and then cultured in the dark at 27° C. The first subcloning takes place 24 h later, and then every fifteen days for 3 months on medium identical to the initiation medium, supplemented with a selective agent. After 3 months, or sometimes earlier, calluses are obtained, the growth of which is not inhibited by the selective agent and which are usually and mainly composed of cells resulting from the division of a cell which has integrated into its genetic inheritance one or more copies of the gene for selection. The frequency of production of such calluses is approximately 0.8 callus per dish bombarded.

These calluses are identified, separated, amplified and then cultured so as to regenerate plantlets, modifying the hormone and osmotic balance of the cells according to the method described by Vain et al. (1989). These plants are then acclimatized in a greenhouse where they can be crossed to obtain hybrids or self-fertilized.

Preferentially, a related protocol is used, the principle of which is described in the work Methods of Molecular Biology: Plant gene transfer and expression protocols (1995, vol. 49, PP 113-123), and in which the immature embryos of the HiII genotype are directly bombarded with particles of gold coated with the PEPC plasmids to be introduced, prepared according to the protocol described by Barcelo and Lazzeri (1995). The steps of transformation, selection of events, maturation and regeneration are substantially similar to those described in the preceding protocol.

2-2—Transformation with *Agrobacterium*

Another technique for transformation which can be used in the context of the invention uses *Agrobacterium tumefaciens*, according to the protocol described by Ishida et al. (1996), in particular using immature embryos taken 10 days after fertilization. All the media used are referenced in the reference cited. The transformation begins with a phase of coculturing in which the immature embryos of the maize plants are brought into contact, for at least 5 minutes, with *Agrobacterium tumefaciens* LBA 4404 containing the superbinary vectors. The superbinary plasmid is the result of homologous recombination between an intermediate vector carrying the T-DNA containing the gene of interest and/or the selection marker derived from the plasmids described in the preceding examples, and the Japan Tobacco vector pSB1 (EP 672 752) which contains: the virB and virG genes of the plasmid pTiBo542 present in the supervirulent strain A281 of *Agrobacterium tumefaciens* (ATCC 37349) and a homologous region found in the intermediate vector, which allows this homologous recombination. The embryos are then placed on LSAs medium for 3 days in the dark and at 25° C. A first selection is performed on the transformed calluses: the embryogenic calluses are transferred onto LSD5 medium containing phosphinotricine at 5 mg/l and cefotaxim at 250 mg/l (elimination or limitation of contamination with *Agrobacterium tumefaciens*). This step is carried out for 2 weeks in the dark and at 25° C. The second selection step is carried out by transferring the embryos which developed on LSD5 medium onto LSD10 medium (phosphinotricine at 10 mg/l) in the presence of cefotaxim, for 3 weeks under the same conditions as previously. The third selection step consists in excising the type I calluses (fragments of 1 to 2 mm) and transferring them, for 3 weeks in the dark and at 25° C., onto LSD10 medium in the presence of cefotaxim.

The plantlets are regenerated by excising the type I calluses which have proliferated and transferring them onto LSZ medium in the presence of phosphinotricine at 5 mg/l and cefotaxim, for 2 weeks at 22° C. and under continuous light.

The plantlets which have regenerated are transferred onto RM+G2 medium containing 100 mg/l of Augmentin for 2 weeks at 22° C. and under continuous light for the development step. The plants obtained are then transferred to a phytotron in order to acclimatize them.

3—Expression 3-1—Extraction of the PEPC from Maize Leaves and Grains

The leaves are removed and immediately frozen in liquid nitrogen. Grinding is done in a mortar cleaned beforehand with 100% ethanol and cooled on ice. A foliar disc 18 mm in diameter is extracted in 200 µl of extraction buffer: Tris-HCl, pH 8.0, 20% glycerol, 10 mM MgCl$_2$, 1 mM EDTA, 1 mM DTT, 2% (w/v) insoluble PVP, Fontainebleau sand and protease inhibitors: 2 mg.l$^{-1}$ leupeptin, 2 mg.l$^{-1}$ chymostatin, 1 mM PMSF and 1 mg.l$^{-1}$ E64. When measurements of the level of phosphorylation of PEPC are planned, the phosphatase inhibitors: okadaic acid, 0.1 mg.l$^{-1}$, and microcystin-LR, 10 nM, are then added. The ground material is then centrifuged at 4° C. for 15 minutes at 20 000 g in order to remove the debris.

The grains are reduced to powder beforehand in a ball mill (Retsch). The proteins are extracted by suspending 100 µl of powder into 400 µl of the buffer described above, on ice. This mixture is vortexed and centrifuged at 4° C. for 15 minutes at 20 000 g in order to remove the debris.

In both cases, the supernatant constitutes the crude extract of soluble proteins. It may be used immediately for measurements of PEPC activity or frozen in liquid nitrogen and stored at −20° C. for subsequent detection by Western blotting.

3-2—Measurements of Expression 3-2-1—Western Blotting

Polyacrylamide gel electrophoresis in the presence of SDS makes it possible to separate the proteins as a function of their molecular mass. The technique is based on that of Laemmli (1970).

Immunodetection of the PEPC on the nitrocellulose membrane takes place, after blocking, by adding a primary antibody which may be:

a) a sorghum $C_4$ PEPC polyclonal antibody prepared according to the method described in Vidal et al. (1980);

b) an anti-phosphorylation site antibody directed against a 23 amino acid synthetic peptide of the N-terminal sequence of sorghum $C_4$ PEPC [ERHHSIDAQLRALAPGKVSEE(YG)] (Crétin et al., 1990), which contains the phosphorylation site. The antibodies were prepared in rabbits and purified by affinity chromatography on protein A Sepharose. These antibodies recognize the phosphorylated or nonphosphorylated forms of the enzyme with the same efficacy. The dilution used is 1/2 000;

c) an anti-C-terminal antibody directed against a 20 amino acid synthetic peptide of the C-terminal sequence of sorghum $C_4$ PEPC [(Y)EDTLILTMKGIAAGMQNTG)]. These antibodies were obtained in rabbits and purified. The dilution used was 1 μl/15 000;

d) a monoclonal antibody produced against the $C_4$ form of sorghum PEPC by the hybridoma technique. More than 400 antibody-producing hybridomas were produced after fusion of immunized mouse screen cells with NS1 myeloma cells. The antibodies 83 and 91 showed very high specificity for sorghum $C_4$ PEPC (Thomas et al., 1987).

The immunodetection of sorghum $C_4$-type PEPC in the plants made it possible to reveal the significant presence of the transgenic protein, in particular with the construct proPEPC-PEPC. In addition, this overexpression correlates with the differences in activity observed between the transgenic plants, and the control plants, up to 2.2 times the level of endogenous PEPC in the leaves.

The construct proHMWG-PEPC (grains) also gave satisfactory results since the level of expression of the PEPC is up to six times greater than the level of expression of the endogenous PEPC in the grains derived from transformed $C_4$-type plants.

3-2-2—Measurements of Activity and Enzymatic Parameters a)—Capacity of the PEPC

The maximum activity of the PEPC is measured using a spectrophotometer (Cary 50, Varian). The principle is based on the coupling of two reactions: β-carboxylation of PEP by PEPC produces oxaloacetate which is reduced to malate by NAD-dependent malate dehydrogenase (MDH). The decrease in absorption at 340 nm due to oxidation of NADH at 30° C. is measured. The reaction medium contains, in a final volume of 1 ml: Hepes/KOH at 100 mM, pH 8, 5 mM $MgCl_2$, 0.2 mM NADH, 5 mM $NaHCO_3$, 5 to 10 mM Na-PEP (Roche) and 3 enzymatic units of NAD-dependent MDH (Roche). The reaction is started by adding 5 to 50 μl of crude leaf or grain protein extract containing the PEPC. One enzymatic unit corresponds to the formation of one μmol of product per minute under the experimental conditions defined above.

Figure 7:
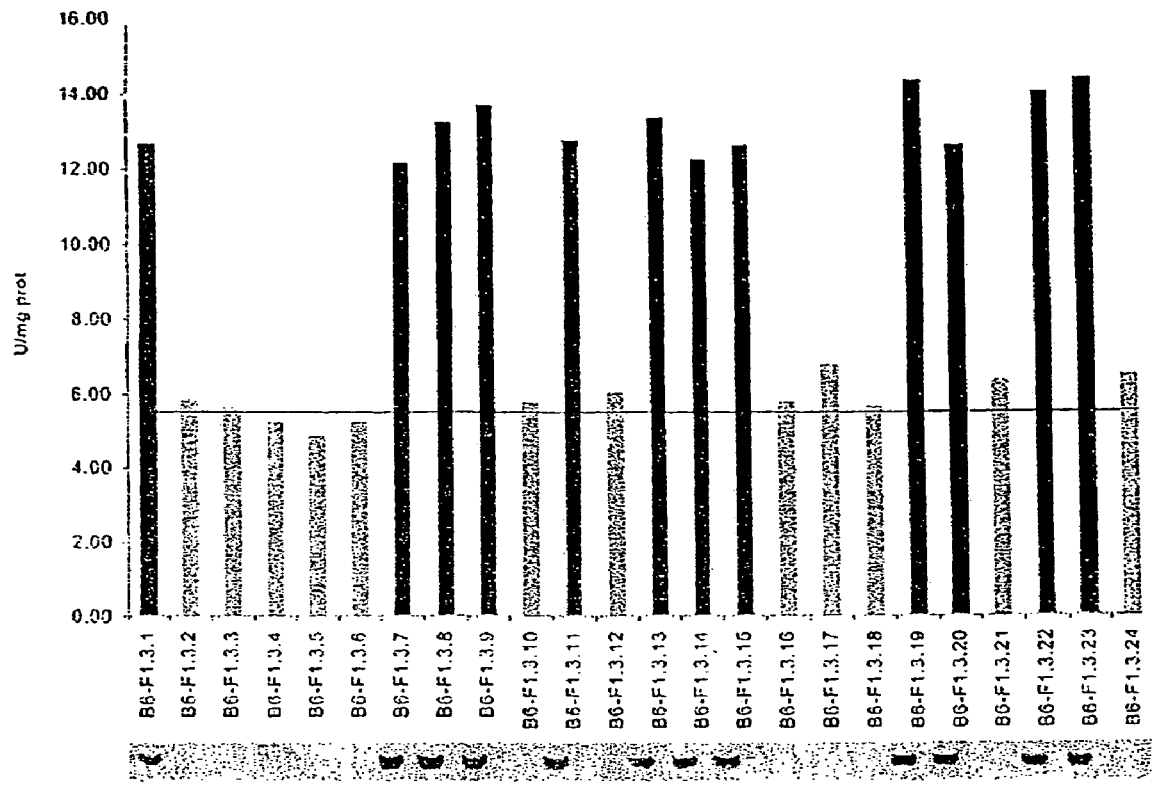
FIG. 7 is a diagram representative of the activity and the immunodetection of PEPC in the soluble protein extracts of leaves from T2 plants transformed with the construct proPEPC-PEPC.

A biochemical study made it possible to demonstrate a 2.2-fold increase in the maximum PEPC enzymatic activity compared with the control level in the leaf (FIG. 7).

Figure 8:
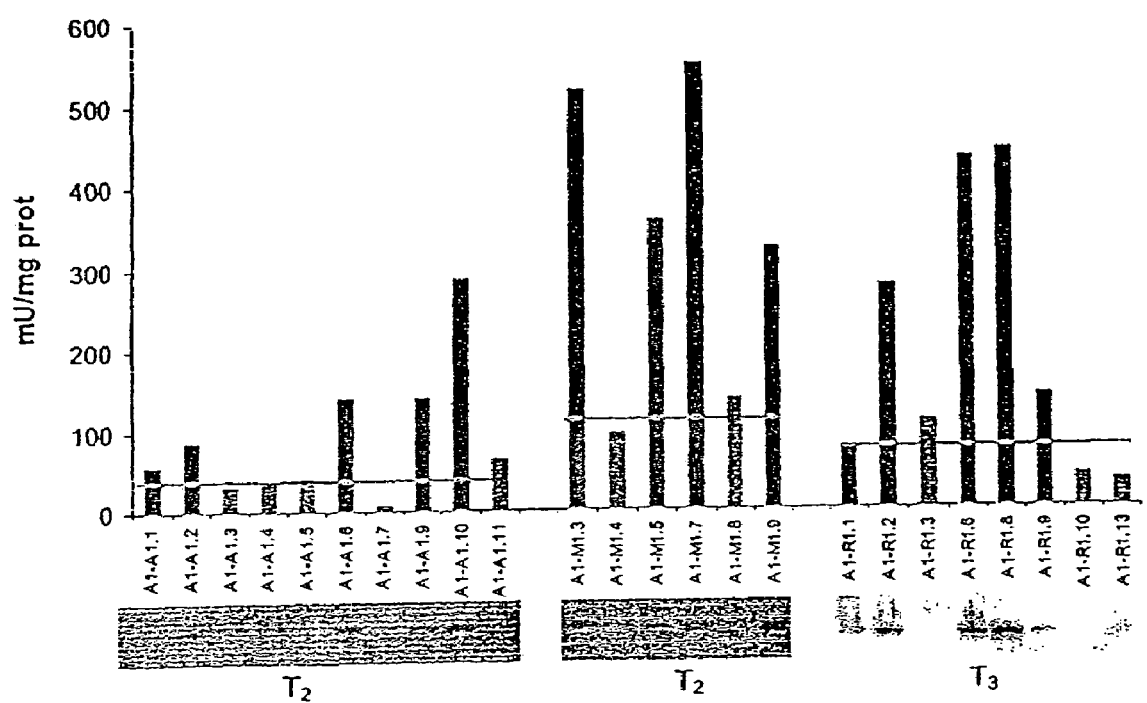
FIG. 8 is a diagram representative of the activity and the immunodetection of the PEPC of soluble protein extracts of individualized grains derived from T2 and T3 ears of plants transformed with the construct proHMWG-PEPC.

For the grain, the enzymatic activity is multiplied up to 6-fold between the transformed grains and the nontransformed grains within the same ear (FIG. 8). Whatever the generation, the proportion of grains which are transformed within the same ear, derived from a cross between a transformed plant and a nontransformed plant or derived from a backcross, ranges from 50 to 100% depending on the number of loci exhibiting the transgene. In most -cases, this proportion is 50% of transformed grains within the same ear.

The increase in PEPC activity correlates quantitatively with the transgenic protein (immunodetection).

More precisely, the level of expression of the enzyme encoded by the transgene (proPEPC~PEPC) in the transformed maize plants was determined by measuring the catalytic activity in foliar protein extracts, and by Western blotting.

50 plants were analysed:

15 plants corresponding to 6 A. tumefaciens transformation events (A6-B, C, D, E, F, I);

35 plants corresponding to 14 biolistic transformation events (B6-A, B, C, D, E, F, G, H, I, J, K, L, M, N).

Some plants (B6-T 1.98183722408633, B6-A4.2) were characterized more precisely. The level of overexpression in terms of PEPC specific activity (at optimal pH and for a PEP concentration of 10 mM) is +112% ±13 (a doubling) for the transformed descendants of the plant B6-T 1.98183722408633, and +17% ±16 for the transgenic descendants of the plant B6-A4.2; the corresponding foliar protein extracts contain the sorghum PEPC (immunodetection).

The inventors noted that the plants having the highest levels of overexpression of recombinant protein (B6-T 0.15244901723741 and B6-A4 transformed by biolistics) are those which have the largest number of copies of the transgene (from 3 to 7 copies).

The inventors also investigated whether the level of activity of the $C_4$ PEPC in the transgenic maize plants is associated with a modification of the level of accumulation of the transcripts.

First, it was verified that the mRNA was effectively produced from the transgene. In Northern blotting, the probe used (65 bp in 5' of the sorghum $C_4$ PEPC cDNA) does not make it possible to distinguish the mRNAs encoding the sorghum and maize enzyme (they are in fact very homologous, including the 5' and 3' untranslated portions). On the other hand, use of the RT-PCR technique demonstrates the specific presence of the transcript in the foliar extracts of total RNA of the plants exhibiting an upward or downward modification of PEPC activity.

Moreover, the Northern blotting experiments (with a probe which hybridizes the two $C_4$ PEPC mRNAs produced) show that the amount of total $C_4$ PEPC transcripts varies in correlation with the amount of the enzyme.

In addition, it was verified that the promoter used (proPEPC: 1 530 bp upstream of the sorghum $C_4$ gene) contains the information for controlling specific expression of the transgene in the mesophyll of the transformed plants which strongly overexpress the sorghum $C_4$ PEPC.

b)—Determination of the $S_{0.5}$ for PEP and of the Sensitivity of the PEPC to Malate The enzymatic constant $S_{0.5}$ is the concentration of PEP which determines a catalytic rate equal to 50% of the maximum rate.

The results show that the $S_{0.5}$ for PEP of PEPC in the grains is significantly greater than that of the enzyme of the control grains, which makes it possible to demonstrate the presence of a (recombinant) $C_4$ form in the transformed grains.

Malate is a physiological inhibitor of PEPC. The activity of the PEPC is measured under suboptimal conditions (3 mM PEP, pH 7.3) in the presence and absence of 1.2 mM L-malate. The results are expressed according to activity in the presence of malate/activity in the absence of malate×100. The dephosphorylated form is more sensitive to inhibition by malate (70%) than the phosphorylated form (approximately 30%). This test makes it possible to estimate the variations in the phosphorylation state of the foliar enzyme when the plant is exposed to various stimuli (light, darkness, stress).

Preliminary studies have shown no significant difference in sensitivity to malate between the plants greatly or slightly overexpressing the recombinant PEPC. Thus, the exogenous PEPC would be phosphorylated in the leaf under light in the same proportions as the endogenous PEPC. This would indicate that, under strong light, the increase in PEPC activity is not compensated for by less phosphorylation.

3-2-3—Assaying Malate

Extraction of metabolites is obtained by grinding 10 mg of material (foliar or grain) in 100 µl of 5% (v/v) perchloric acid with sand and 2% (w/v) of insoluble PVP. The ground material is centrifuged at 20 000 g at 4° C. for 5 minutes. The supernatant is adjusted to a pH of 7.6 with 16 µl of 50% potassium carbonate. The principle of the assay (Roche kit) consists of the oxidation of L-malate to oxaloacetate by malate dehydrogenase (MDH) in the presence of NAD. The reaction is brought to completion in the direction of oxaloacetate formation by coupling this reaction to that of glutamate oxaloacetate transaminase according to the reaction scheme described below.

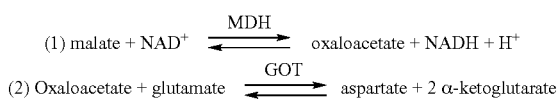

The amount of NADH formed (1 NADH for 1 oxaloacetate) is measured by spectrophotometry at 340 nm, and the following formula makes it possible to calculate the L-malate concentration (C in g.l$^{-1}$) of the extracts analysed:

$$C = \Delta A \times [(V \times MW)/(\epsilon \times d \times v \times 1\,000)]$$

in which:
V=volume of the reaction medium in ml
v=volume of the extract in ml
MW=molecular mass of L-malate in g.mol$^{-1}$
d=optical path length in cm
$\epsilon$=specific absorption coefficient of NADH at 340 nm=6.3 mmol$^{-1}$.cm$^{-1}$ No significant difference in the malate content could be measured between the transformed grains and the control grains. If malate is overproduced in the transformed grains, it is therefore probably metabolized.

3-3—Molecular Studies

Among the transformants, those which exhibit a single locus/single copy insertion (1 copy of the gene of interest and 1 copy of the selection marker) without any undesirable plasmid sequence are preferentially chosen. The Southern technique, with several suitable restriction enzymes and several suitable probes (Southern, 1975), can in particular be used to identify and characterize the insertion into the genome of the plant, thus making it possible to differentiate the transformation events. This methodology in fact makes it possible to demonstrate individual differences in the size of the restriction fragments obtained with a given enzyme and a given probe, corresponding to defined positions on the genome.

The following strategies can be used:
pro HMWG pBIOS 327: ApaI or EcoR V digestion, use of the actin intron probe and of a BAR probe.
proActin pBIOS 326: KpnI digestion, BAR probe. On this construct, the redundancy of the actin promoter and intron does not facilitate the use of a single probe. An RB probe might be used as a second hybridization matrix.
proPEPC pBIOS 356: KpnI digestion, BAR probe and PEPC promoter.

The profiles obtained are those expected.

4—Physiological Measurements in Maize Plants Under Limiting Water and $CO_2$ Conditions 4.1 Assimilation of $CO_2$ and Dry/Fresh Weight Measurements Under Conditions of Water Stress The protocol used comprises the following steps (according to Pelleschi et al. 1997):

The grains (24) of transformed lines are sown on perlite in pots (1 grain/pot) 10 cm in diameter and 25 cm high, which are placed in a greenhouse. The temperature is 26° C. during the daytime and 18° C. at night, the relative humidity is 70% and, if needed, the natural light is supplemented with an artificial light (Philips Sun-T Agro lamp) supplying a minimum of 400 µE. The nutrient solution (Hydrocani C2) is supplemented with a solution of Sequestrene (g/l) making it possible to satisfy the iron requirements of the maize.

Western blotting on a protein extract of the second leaf makes it possible to determine the genotype of the plants and to randomly distribute the segregants in the greenhouse. The water stress is applied when, in 90% of plants, the ligule of the 4th leaf is visible, which is generally observed approximately 15 to 20 days after sowing. The photosynthetic parameters are measured regularly (IRGA CIRAS I device from PP Systems) on each individual for 15 days in order to follow the establishment of the drought on the two batches. At the end of the manipulation, the water potential of the sixth leaf, and the fresh mass and dry mass of the aerial parts are measured, and a sample is frozen for the biochemical analyses.

Measurement of the photosynthetic parameters under the experimental conditions shows that:
the net assimilation of $CO_2$ would increase, on average, by up to 7% compared to the controls, under both normal conditions and conditions of water stress;
at the end of the water stress, the efficiency of water use also increases, by 25% compared to the controls;
after 18 days of water stress, the fresh and dry weights increase by 10% and 20%, respectively, compared to the controls.

Figure 9:
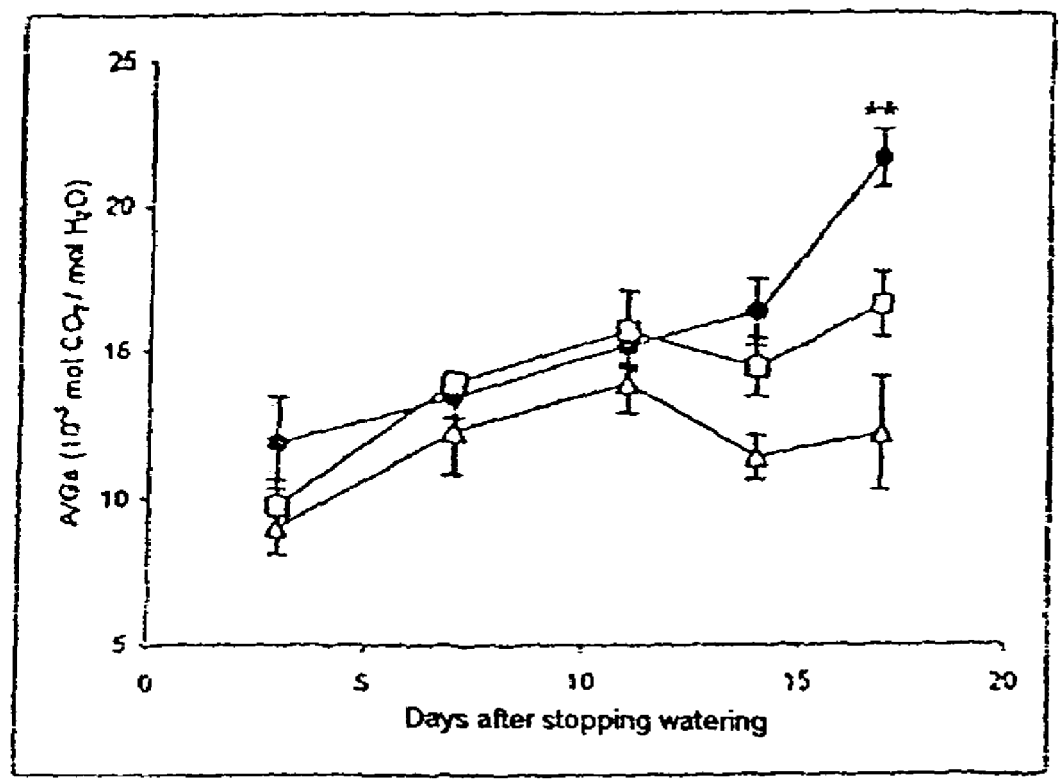
FIG. 9 represents the efficiency of water use (B) of the B6-F1.3 plants.

More precisely, the measurements of the photosynthetic parameters were made on plants subjected to a water constraint in a greenhouse. The automatic watering was stopped as soon as the ligule of the 4th leaf appeared. During the setting up of the water constraint, measurements were made at regular time intervals. For an equal photosynthetic assimilation, the B6-T transgenic plants studied differ very significantly from the control plants with regard to A/Gs (ratio of net assimilation of $CO_2$/stomatic conductance for water), as indicated in FIG. 9. In this figure, when 90% of the plants have reached the ligulate 4th leaf stage, the watering is stopped and the photosynthetic parameters are measured periodically. The points represent the mean of the measurements (±SE); plants with watering maintained (Δ), control plants (•), transformed plants (□). The degree of statistical confidence for the differences observed between the transgenic and nontransgenic plants is indicated by the stars, **$p<0.01$.

From the 10th day of stress, this parameter increases more rapidly for the transgenic plants, reaching a value of 21.6, that is an increase of 30.1%±20.5 (p<0.005). Despite a heterogeneity of germination which induces a variability in the measurements, a second series of experiments on 40 B6-T plants made it possible to confirm the preliminary data (+16%; p>0.2). These results reflect an improvement in water management in the transgenic plants subjected to a drought.

Conversely, in A6-T 0.15244901723741 transgenic plants, which are deficient in $C_4$ PEPC, A and A/Gs are much lower, compared to the control, during the establishment of the water constraint. At the end of the stress, the transgenic plants show a decrease in A and in A/Gs, respectively, of 38%±13.5 (p<0.001) and 47%±4 (p<0.001).

4.2 $CO_2$ Compensation Point and Photosynthetic Efficiency in a $CO_2$-Depleted Atmosphere Culturing is carried out using two pools of grains: the grains are sown onto perlite soaked in a nutrient solution (suitable for maize) or on irradiated compost, and cultured in a greenhouse.

At the 4- to 5-leaf stage, after 8 to 10 days of culture, the Basta test is carried out: the 3rd leaf is daubed (over a surface area of 4 cm$^2$) with a sponge soaked in an aqueous solution of ammonium glufosinate at 0.75 g/l.

The Basta test is read 5 days later: the necrotic leaves reveal the plants which have not been transformed, and these will subsequently be used as a reference (control).

The plants are then transferred into phytotronic chambers and the $CO_2$ compensation point is determined after 20 to 25 days.

$CO_2$ exchange measurements are made for 21 days using plants maintained under the following culture conditions: $CO_2$ concentration of 50 ppm; light from 800 to 1 000 µE.m$^{-2}$.s$^{-1}$; temperature 26° C. during the daytime and 20° C. at night; 80% hygrometry day and night. This subatmospheric concentration of $CO_2$ makes it possible to mimic the effects of a water stress, and in particular the reduction of the opening of the stomata.

At the end of the experiment, the fresh plant mass and the dry weight are determined on all the samples.

Experiments showed that the compensation points of the transgenic plants (whole plant) are 2 to 4 ppm lower (i.e. a 20 to 30% reduction) than those of the nontransformed plants.

More precisely, plants subjected to the experiment were cultured in a greenhouse. A summary of the results is given below.

| B6-T 1 | NT | T | p | T/NT % |
|---|---|---|---|---|
| Number of visible leaves 10 d after sowing | 2.48 ± 0.59 | 2.77 ± 0.42 | p = 0.04 | +11.7* |
| Number of visible leaves 20 d after sowing | 5.58 ± 0.47 | 5.79 ± 0.42 | p = 0.11 | +3.8 |
| Width leaf 4 (cm) | 2.27 ± 0.17 | 2.44 ± 0.25 | p = 0.02 | +7.5* |
| Surface area leaf 4 (cm$^2$) | 36.2 ± 6.0 | 38.7 ± 8.3 | p > 0.2 | +6.9 |
| Width leaf 5 (cm) | 3.34 ± 0.34 | 3.56 ± 0.36 | p = 0.02 | +6.6* |
| Surface area leaf 5 (cm$^2$) | 76.7 ± 18.5 | 82.7 ± 11.8 | p > 0.2 | +7.8 |
| Width leaf 6 after 18 d of stress (cm) | 4.22 ± 0.42 | 4.61 ± 0.17 | p = 0.01 | +9.2* |
| Surface area leaf 6 after 18 d of stress (cm$^2$) | 156 ± 12.3 | 165 ± 24.6 | P > 0.2 | +5.8 |

-continued

| B6-T 1 | NT | T | p | T/NT % |
|---|---|---|---|---|
| Stomatic density 4th leaf (number of stomata · mm$^{-2}$) | 49.0 ± 5.0 | 38.0 ± 5.3 | p = 0.007 | −22** |
| Stomatic density 10th leaf (number of stomata · mm$^{-2}$) | 39.3 ± 1.7 | 36.3 ± 3 | p = 0.03 | −7.6* |
| Fresh weight after 18 d of stress (g) | 22.18 ± 1.74 | 24.49 ± 2.53 | p = 0.03 | +10.4* |
| Dry weight after 18 d of stress (g) | 2.77 ± 0.52 | 3.32 ± 0.50 | p = 0.02 | +19.8* |

It is observed that the transformation manifests itself through pleiotropic effects:

At the beginning of the culture (10 days after seeding), the transgenic B6-T 1 plantlets exhibit a growth advance of approximately 0.3 leaves over the nontransgenic plants. This gap, which is notable at the end of the auxotrophic phase, lessens with the age of the plants since, after 20 days of culturing, the advance is now only 0.2 leaves.

The foliar width is greater in the transformed plants, by 7.5% and 6.6%, respectively, for leaves 4 and 5, under normal culturing conditions; this result is exacerbated (+9.2%) for leaf 6 at the end of a stress lasting 18 days.

The $CO_2$ content of the atmosphere for culturing maize plantlets influences stomatic density. On the 4th and 10th leaf, the increase in PEPC activity correlates with a significant decrease in the number of stomata per unit of surface area.

Finally, all of the photosynthetic and biometric characteristics specific to the transformed plants materialize at the end of the stress through the existence of a significant increase in fresh weight (+10.4%) or in solids (+19.8%) for the transformed plants compared with the controls. This increase is probably the result of a more effective photosynthetic apparatus which, via an integrative phenomenon (exponential in the absolute), allows the plant to increase its rate of growth.

On the other hand, when the photosynthetic PEPC capacity is reduced by 78%, the photosynthetic performances of the maize are considerably impaired (A6-F1.1 plants deficient in C4 PEPC). The leaves are less broad (−10%), the measured dry weight is less (−30%) and the number of stomata has increased (+13.5%) compared with the control plants, with the plants having a weaker appearance, in particular a decrease in sheath dimensions and in pigmentation.

4.3 Other Measurements in the Field

The resistance to water stress of the transformed plants according to the invention, compared with the control plants, can be assessed using various methods of phenotypic, physiological and/or biochemical analyses, for particular irrigation conditions, under normal conditions (conventional growing with watering) and under conditions of water stress.

The grading carried out at the various periods of flowering and of harvesting consist in measuring the effect of the tolerance to stress on grain production, in particular: the percentage fertilization (ratio of the number of grains per ear/number of fertilizable ovules), the number of rows per ear, the number of grains per row, the water content of the grains, the weight of 1 000 grains.

5—Quantitative and Qualitative Modifications of the Protein and Lipid Contents 5.1 Infrared Technique Near-infrared analysis is a spectroscopic technique which uses the natural electromagnetic spectrum. The near-infrared region is the zone in which the spectrum is defined by wavelengths of between 700 nm and 2 500 nm. It is located between the visible region and the medium infrared region. The near-infrared zone is ideal for measuring chemical properties of liquid, solid or gaseous samples or samples in thick suspension. Devices using near-infrared are based on monochromators with a dispersion grating. This technique is relatively precise, rapid and non-destructive. Typical molecules analysed in NIR contain CH, OH and NH bonds, and in particular fatty substances, proteins, starch and soluble sugars.

Changes in balance between the various metabolic pathways for synthesis of organic acids, of fatty acids and of amino acids can be studied using this technique, on the whole grain.

5.2 Element (C, N) Analyser

The method of dry analysis of elements (Dumas) is based on transformation of solid particles into gas by complete and very rapid combustion in an oven at 1 200° C. All the gases produced are entrained out of the oven by a continuous stream of nonreactive gas (helium). Carbon is converted into $CO_2$ during the combustion and the nitrogenous compounds are converted into $N_2$ gas or various nitrogen oxides (NOx). The gases pass over a reducing column composed of copper (600° C.) in which the nitrogen oxides release the oxygen and emerge from the column in the form of $N_2$. The water is retained on a magnesium perchlorate column. The mixture then enters a gas chromatography column (Chromosorb) which separates the nitrogen (eluted first) from the carbon dioxide. Detection by catharometer measures the difference in conductivity between a reference stream (helium) and the stream analysed.

A modification of the total protein content relative to the carbohydrate content can be detected by this method in ground material from each grain.

5.3 Lipid (Fatty Acids and Triglycerides) Content

Total lipids are extracted according to the method of Bligh and Dyer (1959). The ground material from grains is fixed in boiling ethanol and the extraction is then carried out by adding a volume of chloroform, and then of water (1/1/1; V/V/V). A known amount of heptadecanoate (C17:0) is added to the extraction medium. This fatty acid, which is absent in maize, can therefore be used as an internal control.

The fatty acid extract is methylated and the methyl esters are analysed by gas chromatography. The methylation is carried out according to the method of Metcalfe et al. (1966). This technique separates the methyl esters of fatty acids according to the number of carbon atoms and the degree of unsaturation. An integrator makes it possible to calculate the amount of each fatty acid as a function of the internal standard.

A modification of the total lipid content relative to the dry weight can be detected by this method in an extract of each grain.

The increase in the flow of oxaloacetate and then of malate (via PEPC) towards the leucoplasts would appear to lead to an increase in the fatty acid content.

BIBLIOGRAPHIC REFERENCES

An et al. (1986), Plant Physiol, 81:86-91
Armstrong et al. (1994), The Maize Handbook, 665-671
Bandurski and Greiner (1953), J. Biol. Chem., 204:781-786
Barcelo et al. (1995), Methods of Molecular Biology, 49:113-123
Bechtold et al. (1993), Comptes rendus Académie des Sciences Paris Serie 3 [Reports of the Paris Academy of Sciences, Series 3], 316:1194-1199
Blechl et al. (1996), Nat Biotechnol, 14(7):875-879
Bligh et al. (1959), Canadian journal of biochemistry and physiology, 37:911-917
Callis et al. (1987), *Genes Dev.*, 1 : 1183
Cao et al. (1992), Plant Cell Reports
Chupeau et al. (1989), Biotechnology, 7(5):503-508
Coursol et al. (2000), The Plant Journal, 23(4) :497-506
Cretin et al. (1990), Nucleic Acids Res, 11;18(3):658
Cretin et al. (1991), Gene, 99:87-94
Dale et al., 1990, Gene, 91:79-85
Depicker et al., (1982), J. Mol. Appl. Genet., 1, 561-573
Finer et al. (1992). Plant Cell Report, 11:323-328
Franck et al. (1980), Cell, 21:285-294
Fromm M. et al. (1990), Biotechnology, 8:833-839
Gehlen et al. (1996), Plant Mol Biol, 32(5):831-848
Gonzalez et al. (1998), Plant physiology, 116:1249-1258
Guerche et al. (1987), Mol. Gen. Genet., 206:382
Guérineau et al. (1990), Plant Mol Biol, 15:127-136
Hartley, 1988, J. Mol. Biol., 202:913-915
Hatwell et al. (1999), The Plant Journal, 20(3):333-342
Herrera-Estrella et al. (1983) EMBO J, 2:987-995
Hiei et al. (1994). The Plant Journal, 6:271-282
Hoekema et al. (1983). Nature, 303:179-180
Hudspeth et al. (1992), Plant physiology, 98:458-464
Imaizumi et al. (1997), Plant Mol Biol, 34(5) :701-716
Ishida et al. (1996), Nature Biotechnology 14: 754-750
Kasuga et al. (1999), Nature Biotechnology, 17:287-291
Kay et al., (1987) Science, 236:4805
Klein et al. (1987), Nature 327:70-73
Kogami et al. (1994), Transgenic Research, 3:287-296
Ku et al. (1999), Nat Biotechnol, 17(1):76-80
Laemmli et al. (1970), Nature 227:680-685
Lepiniec et al. (1992), Plant Mol Biol, 19(2):339-342
Lipka et al. (1999), Plant Science, 144(2):85-92
McElroy et al. (1990), *Plant Cell*, 2:163-171
McElroy et al. (1991). Molecular and General Genetics, 231 (1), 150-160
Metcalfe et al. (1996), Analytical chemistry, 38:514-515
Morris et al. (1992), *Virology*, 187:633
Neuhaus et al. (1987), Theoretical and applied Genet., 75(1) :30-36
Paul et al. (1992), Plant Molecular Biology, 19(4) :611-622
Pelleschi et al. (1997), Plant Cell Environ, 20:493-503
Robert et al., 1989, Plant Cell, 1:569-578
Sambrook et al. (1989). Molecular cloning, A laboratory manual, 2nd edition cold spring harbor laboratory press
Schocher et al. (1986). Biotechnology 4:1093-1096
Smith et al. (1998), Plant Physiol, 118(1):191-197
Taybi et al. (2000), Plant Physiology, 123(4):1471-1482
Thomas et al. (1987), Biochem Biophys Res Commun 143 (1):170-177
Vain et al. (1989), Plant Cell tissue and organ Culture 18:143-151
Vieira et al. (1982), Gene, 19(3):259-268
Wang et al. (1992), J Biol Chem, 267(24):16759-16762
Watson et al. (1994), ADN recombinant [recombinant DNA], Ed. De Boeck University pp 273-292
White et al. (1990), Nucleic Acids Research 18:1062
Zambryski et al. (1989) Cell, 56, 193-201.

The invention claimed is:

1. A method for producing a $C_4$-type transgenic plant or part of a plant having an improved tolerance to water stress as compared to a non-transgenic plant, comprising:
   (a) transforming at least a $C_4$-type plant's cell by introducing into said plant cell's genome an expression cassette comprising a nucleotide sequence encoding a $C_4$-type phosphoenolpyruvate carboxylase (PEPC) protein derived from sorghum, wherein said nucleotide sequence encoding a C4-type PEPC comprises SEQ ID NO: 1 or a homologous sequence thereof having at least 85% identity of the sequence SEQ ID NO: 1 and having PEPC enzymatic activity;
   (b) culturing said transformed cell to regenerate said plant or part of a plant.

2. The method of claim 1, further comprising identifying and selecting the transformed cells capable of regenerating plants having an improved tolerance to water stress compared with a non-transformed plant.

3. The method of claim 1, wherein said $C_4$-type PEPC protein is overexpressed in said transformed, regenerated plant or part of a plant.

4. The method of claim 1, wherein said nucleotide sequence encodes a $C_4$-type PEPC comprising SEQ ID NO: 1.

5. The method of claim 1, wherein said transformed cell is also transformed with one or more nucleic acids chosen from:
   (a) a nucleic acid encoding a protein component for modulation of the chain of transduction and phosphorylation of said PEPC or
   (b) a nucleic acid encoding another protein of the $C_4$ cycle.

6. The method of claim 1, wherein said expression cassette comprises a promoter which allows constitutive or targeted expression or induced expression under conditions of water stress of said nucleotide sequence encoding a $C_4$-type PEPC.

7. The method of claim 6, wherein said plant or part of a plant, exhibits an increase in expression of said $C_4$-type PEPC protein compared with a non-transformed plant.

8. The method of claim 7, wherein said expression cassette is stably integrated into said plant cell's genome.

9. The method of claim 1, wherein said nucleic acid encoding a $C_4$-type PEPC protein further increases:
   (a) fruit maturation;
   (b) seed filling; and/or
   (c) modified grain filling.

10. The method of claim 5, wherein (b) is pyruvate, phosphate dikinase (PPDK).

11. The method of claim 6, wherein said promoter is the rice actin promoter-intron (RAP-RAI), wheat high molecular weight glutenin (HMWG) promoter, or PEPC promoter.

12. A plant or part of a plant obtained by the method of claim 1.

13. A plant or part of a plant obtained by the method of claim 5.

14. The method of claim 1, wherein said $C_4$-type plants are field crop plants, vegetables, or flowers.

15. The method of claim 14, wherein said field crop plants are maize or sorghum.

16. The method of claim 1, wherein said $C_4$-type transgenic plant or part of a plant has an increased
   (a) fruit maturation;
   (b) seed filling; and/or
   (c) modified grain filling.

17. A method for obtaining a hybrid transgenic plant comprising:
   (a) producing a $C_4$-type transgenic plant or a plant having an improved tolerance to water stress as compared to a non-transgenic plant by the method according to claim 1; and
   (b) crossing the plant obtained in step (a) with a different plant.

18. A transgenic $C_4$-type plant or part of a transgenic $C_4$-type plant according to claim 12, wherein:
   the plant is maize,
   and comprises into its genome an expression cassette comprising a nucleotide sequence encoding a $C_4$-type PEPC derived from sorghum, said nucleotide sequence comprising SEQ ID NO: 1 or a sequence at least 85% identical to SEQ ID NO: 1 and having PEPC enzymatic activity, and
   said $C_4$-type plant has improved tolerance to water stress compared to a non-transgenic plant.

19. The method of claim 11, wherein said PEPC promoter comprises SEQ ID NO: 2.

* * * * *

SEQUENCE LISTING

<160> NUMBER OF SEQ ID NOS: 2

<210> SEQ ID NO 1
<211> LENGTH: 3163
<212> TYPE: DNA
<213> ORGANISM: Sorghum vulgare
<220> FEATURE:
<223> OTHER INFORMATION: PEPC cDNA sequence

<400> SEQUENCE: 1

| | | | | | |
|---|---|---|---|---|---|
| ccatggcgtc | cgagcggcac | cactccatcg | acgcgcagct | ccgtgccctc | gcacccggca | 60 |
| aggtctccga | ggagctcatc | cagtatgacg | ccctgctcgt | cgaccgcttc | ctcgacatcc | 120 |
| tccaggacct | acatggcccc | agccttcgcg | aatttgtcca | ggagtgctac | gaggtgtcgg | 180 |
| ccgactacga | gggcaagaaa | gacacgtcca | agctggggga | gctgggagcc | aagctgacgg | 240 |
| ggctggcccc | cgccgacgcc | atcctggtgg | cgagctccat | cctgcacatg | ctcaacctcg | 300 |
| ccaacctggc | ggaggaagtg | gagctggcgc | accgccgccg | gaacagcaag | ctcaagcacg | 360 |
| gggacttctc | cgacgagggc | tccgccacca | ccgagtccga | catcgaggag | acgtcaagc | 420 |
| gcctcgtgtc | gctcggcaag | accccgcgg | aggtgttcga | ggcgctcaag | aaccagagcg | 480 |
| tcgacctcgt | cttcaccgcg | catcccacgc | agtccgccag | gaggtcgctc | ctgcagaaaa | 540 |
| acgccaggat | ccggaattgt | ctgacgcagc | tgagtgccaa | ggacgtcacg | gtcgaagaca | 600 |
| agaaggagct | cgacgaggct | ctgcacagag | agatccaagc | agctttcaga | actgatgaaa | 660 |
| tcaggagagc | acaacccacc | ccacaggatg | aaatgcgcta | tgggatgagc | tacatccatg | 720 |
| aaactgtatg | gaacggtgtg | cctaagtttt | tgcgccgtgt | ggatacagcc | ctgaagaata | 780 |
| tcggcatcaa | tgagcgcctt | ccctacgatg | ttcctctcat | taagttctgt | tcttggatgg | 840 |
| gtggtgaccg | tgatggaaat | ccaagagtta | ctccggaggt | gacaagagat | gtgtgcttgc | 900 |
| tgtctagaat | gatggctgca | aacttgtaca | tcaatcaggt | cgaagacctg | atgtttgagc | 960 |
| tctctatgtg | gcgctgcaat | gatgagcttc | gtgctcgagc | cgaagaagtc | cagagtactc | 1020 |
| cagcttcaaa | gaaagttacc | aagtattaca | tagaattctg | gaagcaaatt | cccccaaacg | 1080 |
| agccctaccg | ggtgatcctt | ggtgctgtaa | gggacaagtt | atacaacaca | cgcgagcgtg | 1140 |
| cacgccatct | gctggcaact | ggattttctg | aaatttctga | ggacgcggta | tttaccaaga | 1200 |
| tcgaagagtt | ccttgagccc | cttgagctgt | gctacaaatc | cctgtgtgag | tgcggcgaca | 1260 |
| aggccatcgc | cgacgggagc | ctcctggacc | tccttcgcca | ggtgttcacg | ttcggtctct | 1320 |
| ccctggtgaa | gctggacatc | cggcaggagt | cggagcggca | gaccgacgtg | atcgacgcca | 1380 |
| tcaccacgca | cctcggcatc | gggtcgtacc | gctcgtggcc | cgaggacaag | cggatggagt | 1440 |
| ggctggtgtc | ggagctgaaa | ggcaagcgcc | cactgctgcc | cccggacctt | cccatgaccg | 1500 |
| aggagatcgc | cgacgtcatc | ggcgccatgc | gcgtcctggc | cgagctcccg | atcgacagct | 1560 |
| tcggccccta | catcatctcc | atgtgcacgg | cgccctcgga | cgtgctcgcc | gtcgagctcc | 1620 |
| tgcagcgcga | gtgtgcatt | cgccagacgc | tccccgtggt | gccgctgttc | gagaggctgg | 1680 |
| ccgacctgca | ggcggcgccg | gcgtccgtgg | agaagctctt | ctccactgac | tggtacatca | 1740 |
| accacatcaa | cggcaagcag | caggtgatgg | tcggctactc | cgactccggc | aaggacgccg | 1800 |
| gccgcctgtc | cgccggcgtg | cagctgtacg | tggcgcagga | ggagatggcc | aagtggccca | 1860 |
| agaagtacgg | cgtgaagctg | accttgttcc | acggccgcgg | tggcaccgtc | ggcaggggcg | 1920 |
| gtggcccgac | gcacctcgcc | atcctgtccc | agccgccgga | caccatcaac | gggtccatcc | 1980 |

```
gtgtgacggt gcagggcgag gtcatcgagt tcatgttcgg ggaggagaac ctgtgcttcc      2040
agtctctgca gcggttcacg gccgccacgc tggagcacgg catgcacccg ccggtgtctc      2100
ccaagcccga gtggcgcaag ctcatggagg agatggccgt cgtcgccacg gaggagtacc      2160
gctccgtcgt cgtcaaggag ccgcgattcg tcgagtactt cagatcggct acccctgaga      2220
ctgagtacgg gaagatgaac atcggcagca ggccagccaa gaggaggccg gcggcggca      2280 tcaccaccct gcgtgccatc ccctggatct tctcgtggac acagacgagg ttccacctcc      2340
ccgtgtggct gggagtcggc gccgccttca gtgggccat cgacaaggac atcaagaact       2400
tccagaagct caaggagatg tacaacgagt ggccattctt cagggtcacc ctggacctgc      2460
tggagatggt tttcgccaag ggagaccctg gcattgccgg cttgtacgac gagctgcttg      2520
tcgccgagga actcaagccc tttgggaagc agctcaggga caaatacgtg gagacacagc      2580
agcttctcct acagatcgct ggcacaagg acattcttga aggcgatcct tacctgaagc       2640
aggggctgcg tctgcgcaat ccctacatca ccaccctgaa cgtgttccag gcctacacgc      2700
tgaagcggat aagggacccc agcttcaagg tgacgccgca gccgccgctg tccaaggagt     2760
tcgccgacga gaacaagccc gccggactgg tgaagctgaa cggcgagcga gtaccgccgg     2820
ggctggaaga cacgctcatc ctcaccatga agggtatcgc cgccggcatg cagaacaccg    2880
gctaggccgc ttccccttca ctcacctgca gagtactgca cggcaataat aatcacagct    2940
tccggatggt ggcgttttgt cagttttgga tggagatgct gaaaactgac caccctgtt     3000 ttcactatat gcatgtttat gtaatttcct cggctttggc ctctttatat ttttcactct    3060
tgttgtgaag tccaagtgga aaatcttggc atcttaaata tattgtaata atgaacatca    3120
tataatctac aaatttacta ttatgtatta aaaaaaaaaa aaa                        3163

<210> SEQ ID NO 2
<211> LENGTH: 1530
<212> TYPE: DNA
<213> ORGANISM: Sorghum vulgare
<220> FEATURE:
<223> OTHER INFORMATION: PEPC promotor sequence

<400> SEQUENCE: 2
atggttgatc cagatctcga cctactcgat ctaatacatg ttgacagcaa gctgaggatc       60
gggacatgta ataaggagtt aggagatgtg gtatggtact aaatgcaagg tcaaaattcg      120 atgcttttc cgtgctcaac tattaactag tattattacc taattttac ttgtgatgac       180 aactaatgca tcgagccaca attcagtaaa tacttacatt aatttaagca tatgtatagt      240
atatacattt ccaattcttc ttttttgtgt ggagatccac gacgatgcaa gttgctcctc      300
ccaacccaaa tccacctctc tcttaaatcc gcgtatcttc accaccacca gctgctacac      360
atcgtattgt ccaaatctgt gtcggcttga cccagtgatg tgcgcgctag atttggcagc      420
gcctgaatgc agtgcagcca cctgtatggt acccttggta gagtaacaac acccttatcc      480
ctacggcagc catgtatgac ccttatccct acggcagcca tgtataccaa tacctttctt      540
tgaaccacaa aattatagtc catatcctta accacaagtt catttttgt tcccggtct       600 cgtaaggaaa ttaagttctg tttccacaat ttacatggat ataggacatc tatgttccta     660
acattaacat tactggataa caggcaccct ctcctccaca ccctgcaaag ccttcctcca     720
gcgccatgca tcctccgttg ctaacagaca cctctctcca catcgcgtgc aagcaaacct    780
ccaaattcta ccgatcccca gaatccggcc ttgactgcaa acagacaccc ctctccccat    840
```

```
cctgcaaacc catcagccaa ccgaataaca caagaaggca ggtgagcagt gacaaagcac    900
gtcaacagca gcaaagccaa gccaaaaacg atccaggagc aaggtgcggc cgcagctctc    960
ccggtcccct ttgcggttac cactagctaa gaatgaagat ggtactctaa atgcatactt   1020
gcgcggtttt tctctagtct aacttaataa actaaataaa caatttcttt cttattttt    1080 taatttagtt cgtttagtta gactagagaa gaaccacgag gagttatttg aagcatcgtc   1140
cccatcctta ccactagcta gcactagcag acaccctct ccacgtcctg caaacaggca    1200
atattagcca gcggaataac acaagcaggc aagtgcgcag tgacaaagta cgtccacagc   1260
agcgatccca gccaaaagca gcgtagccac agccgcgcgc agctctcggc tacccttacc   1320
gccgatcaca tgcatgcctt tccaatcccg cgtgcacacg ccgaccacac actcgccaac   1380
tccccatccc tatttgaagc caccggccgg cgccctgcat tgatcaatca actcgcagca   1440
gaggagcagc acgagcaaca cgccgcgccg cgctccaacc atctccagct tcgttcgcgc   1500
ttcccggccc actcccggc cgccgccgcc                                     1530
```